(12) United States Patent
Dubrow

(10) Patent No.: US 7,344,617 B2
(45) Date of Patent: *Mar. 18, 2008

(54) STRUCTURES, SYSTEMS AND METHODS FOR JOINING ARTICLES AND MATERIALS AND USES THEREFOR

(75) Inventor: Robert Dubrow, San Carlos, CA (US)

(73) Assignee: Nanosys, Inc., Palo Alto, CA (US)

( * ) Notice: Subject to any disclaimer, the term of this patent is extended or adjusted under 35 U.S.C. 154(b) by 74 days.

This patent is subject to a terminal disclaimer.

(21) Appl. No.: 11/374,906

(22) Filed: Mar. 14, 2006

(65) Prior Publication Data

US 2006/0165952 A1    Jul. 27, 2006

Related U.S. Application Data

(63) Continuation of application No. 10/661,381, filed on Sep. 12, 2003, now Pat. No. 7,056,409.

(60) Provisional application No. 60/463,766, filed on Apr. 17, 2003.

(51) Int. Cl.
*B32B 37/00* (2006.01)

(52) U.S. Cl. ............ 156/276; 156/60; 156/306.3; 977/902; 977/931; 977/962; 977/963

(58) Field of Classification Search ............ 156/276, 156/306.3; 977/902, 931, 961, 962, 963
See application file for complete search history.

(56) References Cited

U.S. PATENT DOCUMENTS

| 5,196,396 | A | 3/1993 | Lieber |
|---|---|---|---|
| 5,252,835 | A | 10/1993 | Lieber et al. |
| 5,332,910 | A | 7/1994 | Haraguchi et al. |
| 5,505,928 | A | 4/1996 | Alivisatos et al. |
| 5,690,807 | A | 11/1997 | Clark, Jr. et al. |
| 5,751,018 | A | 5/1998 | Alivisatos et al. |
| 5,840,435 | A | 11/1998 | Lieber et al. |
| 5,897,945 | A | 4/1999 | Lieber et al. |
| 5,976,957 | A | 11/1999 | Westwater et al. |
| 5,990,479 | A | 11/1999 | Weiss et al. |
| 5,997,832 | A | 12/1999 | Lieber et al. |
| 6,036,774 | A | 3/2000 | Lieber et al. |
| 6,048,616 | A | 4/2000 | Gallagher et al. |
| 6,106,913 | A | 8/2000 | Scardino et al. |

(Continued)

FOREIGN PATENT DOCUMENTS

| WO | WO-9629629 | 9/1996 |
|---|---|---|
| WO | WO-9918893 | 4/1999 |
| WO | WO-9940812 | 8/1999 |
| WO | WO-0149776 | 7/2001 |

(Continued)

OTHER PUBLICATIONS

Autumn, K. et al., "Adhesive force of a single gecko foot-hair" Nature (2000) 405:681-685.

(Continued)

*Primary Examiner*—Melvin Mayes
(74) *Attorney, Agent, or Firm*—Andrew L Filler

(57) ABSTRACT

This invention provides novel nanofibers and nanofiber structures which posses adherent properties, as well as the use of such nanofibers and nanofiber comprising structures in the coupling and/or joining together of articles or material.

14 Claims, 5 Drawing Sheets

U.S. PATENT DOCUMENTS

| | | | |
|---|---|---|---|
| 6,130,143 | A | 10/2000 | Westwater et al. |
| 6,136,156 | A | 10/2000 | El-Shall et al. |
| 6,159,742 | A | 12/2000 | Lieber et al. |
| 6,190,634 | B1 | 2/2001 | Lieber et al. |
| 6,207,229 | B1 | 3/2001 | Bawendi et al. |
| 6,225,198 | B1 | 5/2001 | Alivisatos et al. |
| 6,265,333 | B1 | 7/2001 | Dzenis et al. |
| 6,268,041 | B1 | 7/2001 | Goldstein |
| 6,270,347 | B1 | 8/2001 | Webster et al. |
| 6,306,736 | B1 | 10/2001 | Alivisatos et al. |
| 6,313,015 | B1 | 11/2001 | Lee et al. |
| 6,322,895 | B1 | 11/2001 | Canham |
| 6,359,288 | B1 | 3/2002 | Ying et al. |
| 6,413,489 | B1 | 7/2002 | Ying et al. |
| 6,666,214 | B2 | 12/2003 | Canham |
| 6,669,256 | B2 | 12/2003 | Nakayama et al. |
| 6,670,179 | B1 | 12/2003 | Mattson et al. |
| 6,720,240 | B2 | 4/2004 | Gole et al. |
| 7,056,409 | B2 * | 6/2006 | Dubrow ............... 156/276 |
| 7,067,328 | B2 * | 6/2006 | Dubrow et al. ............. 438/1 |
| 7,074,294 | B2 * | 7/2006 | Dubrow ............... 156/276 |
| 7,132,161 | B2 * | 11/2006 | Knowles et al. ........... 428/364 |
| 7,181,811 | B1 * | 2/2007 | Tomanek et al. ............. 24/442 |
| 2002/0037383 | A1 | 3/2002 | Spillman et al. |
| 2002/0049495 | A1 | 4/2002 | Kutryk et al. |
| 2002/0090725 | A1 | 7/2002 | Simpson et al. |
| 2002/0130311 | A1 | 9/2002 | Lieber et al. |
| 2002/0167118 | A1 | 11/2002 | Billiet et al. |
| 2002/0172963 | A1 | 11/2002 | Kelley et al. |
| 2003/0032892 | A1 | 2/2003 | Erlach et al. |
| 2003/0059742 | A1 | 3/2003 | Webster et al. |
| 2003/0065355 | A1 | 4/2003 | Weber |
| 2003/0089899 | A1 | 5/2003 | Lieber et al. |
| 2003/0093107 | A1 | 5/2003 | Parsonage et al. |
| 2003/0124312 | A1 | 7/2003 | Autumn |
| 2003/0195611 | A1 | 10/2003 | Greenhalgh et al. |
| 2003/0208888 | A1 | 11/2003 | Fearing et al. |
| 2003/0229393 | A1 | 12/2003 | Kutryk et al. |
| 2004/0005454 | A1 | 1/2004 | Full et al. |
| 2004/0009598 | A1 | 1/2004 | Hench et al. |
| 2004/0023317 | A1 | 2/2004 | Motamedi et al. |
| 2004/0026684 | A1 | 2/2004 | Empedocles |
| 2004/0052867 | A1 | 3/2004 | Canham |
| 2004/0071870 | A1 | 4/2004 | Knowles et al. |
| 2004/0076681 | A1 | 4/2004 | Dennis et al. |
| 2004/0098023 | A1 | 5/2004 | Lee et al. |
| 2004/0106203 | A1 | 6/2004 | Stasiak et al. |
| 2004/0115239 | A1 | 6/2004 | Shastri et al. |
| 2004/0250950 | A1 | 12/2004 | Dubrow et al. |
| 2005/0072509 | A1 | 4/2005 | Full et al. |
| 2005/0096509 | A1 | 5/2005 | Olson |

FOREIGN PATENT DOCUMENTS

| | | |
|---|---|---|
| WO | WO-02080280 | 10/2002 |
| WO | WO-0217362 | 2/2003 |
| WO | WO-03095190 | 11/2003 |
| WO | WO-03097702 | 11/2003 |
| WO | WO-03099951 | 12/2003 |
| WO | WO-03102099 | 12/2003 |

OTHER PUBLICATIONS

Bjork, M.T. et al., "One-dimensional steeplechase for electrons realized" Nano Letters (2002) 2:86-89.

Cao, Y.W. et al., "Growth and properties of semiconductor core/shell nanocrystals witn InAs cores" J. Am. Chem. Soc. (2000) 122:9692-9702.

Chen, I.W. et al., "Sintering dense nanocrystalline ceramics without final-stage grain growth" Nature (2000) 404(6774):168-171.

Choi, H. et al., "Surface-modified silica colloid for diagnostic imaging" J. Colloid interface Sci (2003) 258(2):435-437.

Cui, Y. et al. "Doping and electrical transport in silicon nanowires" J. Phys. Chem. B (2000) 104(22):5213-5216.

Cui et al., "Functional nanoscale electronic devices assembled using silicon nanowire building blocks" Science (2001) 291:851-853.

Cui et al., "Nanowire nanosensors for highly sensitive and selective detection of biological and chemical species" Science (2001) 293:1289-1292.

Cui, Y. et al. "Diameter-controlled synthesis of single-crystal silicon nanowires" (2001) Appl. Phys. Letts. 78(15):2214-2216.

Dabbousi, B.O. et al., "(cdSe)ZnS core-shell quantum dots: Synthesis and characterization of a sizze series of highly luminescent nanocrystallites" J. Phys. Chem. B (1997) 101(46):9463-9475.

Davis, D.H. et al., "Immobilization of RGD to <111> silicon surfaces for enhanced cell adhesion and proliferation" Biomaterials (2002) 23:4019-4027.

Duan, X. et al., "General synthesis of compound semiconductor nanowires" Adv. Mater. (2000) 12(4):298-302.

Duan, X. et al., "Single-nanowire electrically driven lasers" Nature (2003) 421:241-245.

Geim, A.K. et al., "Microfabricated adhesive mimicking gecko foot-hair" Nature Materials (2003) 2:461-463.

Greene, L.E. et al., "Low-Temperature Wafer-Scale Production of ZnO Nanowire Arrays" Angew. Chem. Int. Ed. (2003) 42:3031-3034.

Gudiksen, M.S. et al., "Diameter-selective synthesis of semiconductor nanowires" J. Am. Chem. Soc. (2000) 122:8801-8802.

Gudiksen, M.S. et al., "Synthetic control of the diameter and length of single crystal semiconductor nanowires" J. Phys. Chem. (2001) 105(19):4062-4064.

Gudiksen, M.S. et al., "Growth of nanowire superlattice structures for nanoscale photonics and electronics" Nature (2002) 415:617-620.

Hanekamp C. et al., "Randomized comparison of balloon angioplasty versus silicon carbon-coated stent implantation for de novo lesions in small coronary arteries" Am. J. Cardiol. (2004) 93(10):1233-1237.

Haraguchi, K. et al., "Polarization dependence of light emitted from GaAs p-n junctions in quantum wire crystals" J. Appl. Phys. (1994) 75(8):4220-4225.

Haraguchi, K. et al., "Self organized fabrication of planar GaAs nanowhisker arrays" Appl. Phys. Lett (1996) 69(3):386-387.

Hiruma, K. et al., "GaAs free-standing auntum-sized wires" J. Appl. Phys. (1993) 74(5):3162-3171.

Huang et al., "Integrated optoelectronics assembled from semiconductor nanowires" Abstracts of Papers of the ACS (2002) 224:U308.

Jun, Y-W. et al., "Controlled synthesis of multi-armed CdS nanorod architectures using monosurfactant system" J. Am. Chem. Soc. (2001) 123(21):5150-5151.

Kong, J. et al., "Chemical vapor deposition of methane for single-walled carbon nanotubes," Chem. Phys. Lett (1998) 292:567-574.

Kong, J. et al., "Synthesis of individual single-walled carbon nanotubes on patterned silicon wafers" Nature (1998) 395:878-881.

Liu, C. et al., "Sol-Gel synthesis of free-standing ferroelectric lead zirconate titanate nanoparticles" J. Am. Chem. Soc. (2001) 123(18):4344-4345.

Manna, L. et al., "Synthesis of soluble and processable rod-, arrow-, teardrop-, and tetrapod-shaped CdSe nanocrystals" J. Am. Chem. Soc. (2000) 122:12700-12706.

Manna, L. et al., "Epitaxial growth and photochemical annealing of graded CdS/ZnS shells on colloidal CdSe nanorods" J. Am. Chem. Soc. (2002) 124:7136-7145.

Morales, A.M. et al., "A laser ablation method for the synthesis of crystalline semiconductor nanowires" Science (1998) 279(9):208-211.

Peng, X. et al., "Epitaxial growth of highly luminescent CsDe/CdS core/shell nanocrystals with photostability and electronic accessibility" J. Am. Chem. Soc. (1997) 119(30):7019-7029.

Peng, X. et al., "Shape control of CdSe nanocrystals" Nature (2000) 404:59-61.

Price, R.L. et al., "Nanometer surface roughness increases select osteoblast adhesion on carbon nanofiber compacts" J. Biomed. Mat. Res. (2004) 70A(1):129-138.

Puntes, V.F. et al., "Colloidal nanocrystal shape and size control: The case of cobalt" Science (2001) 291:2115-2117.

Schon, J.H. et al., "Self-assembled monolayer organic field effect transistors" Nature (2001) 413:713-716.

Shastri, V.P., "Non-degradable biocompatible polymers in medicine: past, present and future" Curr Pharm. Biotechnol. (2003) 4(5):331-337.

Silva, G.A. et al., "Selective differentiation of neural progenitor cells by high-epitope density nanfibers" Science (2004) 303:1352-1355.

Thess, A. et al., "Crystalline ropes of metallic carbon nanotubes" Science (1996) 273:483-487.

Urban, J.J. et al., "Synthesis of single-crystalline perovskite nanorods composed of varium titanate and strontium titanate" J. Am. Chem. Soc. (2002) 124(7):1186-1187.

Webster, T.J. et al., "Nano-biotechnology: carbon nanofibres as improved neural and orthopaedic implants" Nanotechnology (2004) 15:48-54.

Webster, T.J. et al., "Increased osteoblast adhesion on nanophase metals: Ti, Ti6A14V, and CoCrMo" Biomaterials (2004) 25:4731-4739.

Wu, Y. et al., "Block-by-block growth of single-crystalline Si/SiGe superlattice nanowires" Nano Letters (2002) 2(2):83-86.

Xu, H. et al., "Room-temperature preparation and characterization of poly(ethylene glycol)-coated silica nanoparticles for biomedical applications" J. Biomed. Mat. Res. (2003) 66A(4):870-879.

Xu, H. et al., "Strong and bioactive composites containing nano-silica-fused whiskers for bone repair" Biomaterials (2004) 25:4615-4626.

Yazawa, M. et al., "Semiconductor nanowhiskers" Adv. Mater. (1993) 5(7/8):577-580.

Yun, W.S. et al., "Ferroelectric properties of individual barium titanate nanowires investigated by scanned probe microscopy" Nano Letters (2002) 2(2):447-450.

Zhou, C. et al., "Nanoscale metal/self-assumbed monolayer/metal heterostructures" Appl. Phys. Lett (1997) 71(5):611-613.

Zhou, X.T. et al., "Silicon nanowires as chemical sensors" Chem. Phys. Lett. (2003) 369:220-224.

\* cited by examiner

STRUCTURES, SYSTEMS AND METHODS FOR JOINING ARTICLES AND MATERIALS AND USES THEREFOR

CROSS-REFERENCE TO RELATED APPLICATIONS

This application is a continuation of U.S. patent application Ser. No. 10/661,381, filed Sep. 12, 2003, which claims the benefit of U.S. Provisional Application No. 60/463,766 filed Apr. 17, 2003, entitled "STRUCTURES, SYSTEMS AND METHODS FOR JOINING ARTICLES AND MATERIALS AND USES THEREFOR." These prior applications are hereby incorporated by reference in their entirety.

FIELD OF THE INVENTION

The invention relates primarily to the field of nanotechnology. More specifically, the invention pertains to nanofibers and nanofiber structures which posses adherent properties, as well as to the use of such nanofibers and nanofiber comprising structures in the coupling and/or joining together of articles or materials.

BACKGROUND OF THE INVENTION

Joining together of articles and/or materials has been common for at least thousands of years. Such joining has typically been achieved through use of adhesives of various types, e.g., exogenous substances applied between articles or materials to be joined which adhere to both of the articles or materials and, thus, join them. Today, modern adhesives are an integral part of life. Typical modern adhesives comprise what are known as contact adhesives. Such contact adhesives are usually based upon variations of soft sticky polymers of varying viscosity, which conform to surfaces and adhere through van der Waals forces, thereby joining surfaces/materials.

While such typical adhesives are quite useful, they do have a number of limitations. For example, the layer of adhesive necessary to join surfaces can be inconveniently thick (e.g., from hundreds of microns to millimeters, etc.). While that might be acceptable in some situations, it is quite inappropriate in others. Adhesives can also often leave messy residues. Additionally, adhesives can leak, spread or volatilize from their area of application into other nearby areas where they are not desired. Such spreading can not only result in unintended joining of materials, but can also result in chemical or physical contamination of such other areas.

Furthermore, while a wide range of adhesive compounds exist, the majority of them have a (sometimes limited) range of parameters necessary for their use. For example, some adhesives do not work above a certain ambient temperature (e.g., the polymers become too fluidic and the adhesive either loses much of its adherent property or leaks away). Other adhesives do not work below a certain temperature (e.g., the adhesive becomes brittle and cracks). Yet other adhesives do not adhere in the presence of water, organic solvents and/or vacuum, etc., while other adhesives require such conditions.

In addition to exogenous adhesive compounds, other adherents such as "hook and loop" or "touch fasteners'" e.g., Velcro®, have more recently been used to join materials together. However, such systems also are problematic in typically requiring two groups of specifically shaped fiber groups.

In the context of the above background, research on new adherents and methods of adhesion has been intrigued by examples of adhesion and adherent ability in the natural world. For example, the ability of geckos, spiders and flies to adhere to seemingly shear surfaces has long fascinated researchers. Geckos' ability to stick to surfaces without the use of an adhesive substance (such as a polymer, etc.) has been under intense scrutiny recently as a model for adhesion.

A welcome addition to the art would be an adherent material or surface or a method of adhesion which could be modified to fit different environmental conditions and parameters, which would not migrate to unwanted areas, which would not necessarily require two dedicated surfaces, and which would require no external application of resins, carriers, etc. The current invention provides these and other benefits which will be apparent upon examination of the following.

SUMMARY OF THE INVENTION

In some aspects the current invention comprises a method of adhering two or more surfaces together by providing a first surface (which has a plurality of nanofibers attached to it), providing at least a second surface, and contacting the surfaces together, thereby adhering them to each other. In some embodiments herein, the surfaces and the plurality of nanofibers can optionally comprise such materials as, e.g., silicon, glass, quartz, plastic, metal, polymers, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, SiO1, SiO2, silicon carbide, silicon nitride, polyacrylonitrile (PAN), polyetherketone, polyimide, an aromatic polymer, or an aliphatic polymer. The contacting of the surfaces, optionally creates van der Waals attraction between the surfaces. In some embodiments herein such attraction comprises from at least about 0.1 newton per centimeter$^2$ to at least about 100 newtons per centimeter$^2$, from at least about 0.5 newton per centimeter$^2$ to at least about 50 newtons per centimeter$^2$, from at least about 1 newton per centimeter$^2$ to at least about 25 newtons per centimeter$^2$, or from at least about 2 newtons per centimeter$^2$ to at least about 10 newtons per centimeter$^2$. Alternatively and/or additionally, the contact of the surfaces creates friction forces between the surfaces which, in typical embodiments, are greater than friction forces that would result form contact of similar surfaces, but without the nanofibers. Furthermore, the first surface of some such embodiments comprises a surface density of members of the plurality of nanofibers from at least about 1 nanofiber per micron$^2$ to 1000 or more nanofibers per micron$^2$; from at least about 5 nanofibers per micron$^2$ to 500 or more nanofibers per micron$^2$; from at least about 10 nanofibers per micron$^2$ to 250 or more nanofibers per micron$^2$; or from at least about 50 nanofibers per micron$^2$ to 100 or more nanofibers per micron$^2$. Additionally, in other embodiments, the first surface and the at least second surface are composed of the same material.

Furthermore, in yet other embodiments, the nanofibers are composed of the same material as one or more of the first or second substrates. Other embodiments include where the nanofibers are hollow nanotubular structures. In yet other embodiments substantially all nanofibers comprise one or more associated moiety (optionally a coating composed of the one or more associated moiety) which can be a functional moiety in some embodiments. In some such embodiments the functional moiety can increase van der Waals attraction between the nanofiber and the at least second surface (i.e., so that the attraction between the nanofiber and the second surface is greater than the van der Waals attraction between the nanofiber and the at least second surface in the absence of the moiety) or can increase friction forces between the nanofiber and the at least second surface (i.e., so that when a normal force is applied, the friction between the nanofiber and the second surface is greater than the friction between the nanofiber and the at least second surface in the absence of the moiety). The functional moiety can include or comprise a covalent bond. (e.g., create a covalent bond) between the nanofiber and the at least second surface. In yet other embodiments, not only does the first surface optionally comprise a plurality of nanofibers, but the at least second surface can comprise a plurality of nanofibers attached thereto also. Also in some embodiments, the nanofibers comprise curled or curved nanofibers that touch one or more surface at more than one point and/or which touch one or more surface by contacting the surface with the side of the nanofiber instead of, or in addition to, the tip of the nanofiber.

In other aspects, the invention comprises a method of joining two or more articles. Such method comprises providing a first article (with at least a first surface comprising a plurality of nanofibers attached to it or associated with it), providing at least a second article having at least a first surface, and mating the first surface of the second article with the plurality of nanofibers on the first surface of the first article (so that the nanofibers contact the first surface of the second article at a plurality of contact points) whereby forces between the nanofibers and the first surface of the second article adhere the first article to the second article. In some typical embodiments such forces comprise van der Waals forces. In other typical embodiments, such forces can alternatively or additionally comprise friction when a normal force is applied. Such embodiments optionally comprise a density of contact points per unit area (i.e., the contact density or intimate contact area, etc.) of the second surface. The density of contact points can optionally comprise contact of from at least about 1 nanofiber per micron$^2$ to 2000 or more nanofibers per micron$^2$; from at least about 5 nanofiber per micron$^2$ to 1000 or more nanofibers per micron$^2$; from at least about 10 nanofiber per micron$^2$ to 500 or more nanofibers per micron$^2$; from at least about 50 nanofiber per micron$^2$ to 250 or more nanofibers per micron$^2$; from at least about 75 nanofiber per micron$^2$ to 150 or more nanofibers per micron$^2$. Of course, in some embodiments, e.g., when nanofibers curve and touch a surface more than once, the measurements are typically nanofiber contacts per square micron of the surface. In some embodiments the plurality of contact points (i.e., the contact density or intimate contact area, etc.) comprises a percent contact area of the second surface, which can optionally comprise from about 0.1% to at least about 50% or more; from about 0.5% to at least about 40% or more; from about 1% to at least about 30% or more; from about 2% to at least about 20% or more; or from about 5% to at least about 10% or more of the area of the second surface. Furthermore, embodiments herein can optionally comprise a plurality of contact points comprising a density of contact points per unit area of the second surface and comprising a percent contact area of the second surface. Thus, the density of contact points can comprise contact of from at least about 1 nanofiber per micron$^2$ to about 2000 or more nanofibers per micron$^2$, from at least about 5 nanofiber per micron$^2$ to about 1000 or more nanofibers per micron$^2$, from at least about 10 nanofiber per micron$^2$ to about 500 or more nanofibers per micron$^2$, from at least about 50 nanofiber per micron$^2$ to about 250 or more nanofibers per micron$^2$, or from at least about 75 nanofibers per micron$^2$ to about 150 or more nanofibers per micron$^2$, and, can also comprise a percent contact area of the second surface from about 0.1% to at least about 50% or more, from about 0.5% to at least about 40% or more, from about 1% to at least about 30% or more, from about 2% to at least about 20% or more, or from about 5% to at least about 10% or more.

In other aspects, the present invention comprises a method of joining two or more articles, by providing a first article having at least a first surface, providing at least a second article having at least a first surface; and providing a layer of nanofibers disposed between the first surface of the first article and the first surface of the at least second article, whereby the nanofibers contact the first surface of the first article and the first surface of the at least second article at a plurality of contact points, so that forces between the nanofibers and the first surface of the first article and the first surface of the at least second article adhere the articles together. In typical embodiments such forces comprise van der Waals forces and/or friction forces (e.g., when a normal force is applied to the surfaces).

In yet other aspects herein, the invention comprises an adhesive device comprising a first article (having at least a first surface), at least a second article (having at least a first surface) and, a layer of nanofibers disposed between the first surface of the first article and the first surface of the at least second article, whereby the nanofibers contact the first surface of the first article and the first surface of the at least second article at a plurality of contact points, such that forces between the nanofibers and the first surface of the first article and the first surface of the at least second article adhere the articles together. In typical embodiments such forces comprise van der Waals forces. Such devices also include wherein one or more of the first surface and the at least second surface comprise a plurality of nanofibers, and also wherein physical contact between the first and at least second substrate produces a van der Waals attraction between the surfaces. In some embodiments, such attraction can comprise from at least about 0.1 newton per centimeter$^2$ to at least about 100 newtons per centimeter$^2$, from at least about 0.5 newton per centimeter$^2$ to at least about 50 newtons per centimeter$^2$, from at least about 1 newton per centimeter$^2$ to at least about 25 newtons per centimeters$^2$, or from at least about 2 newtons per centimeter$^2$ to at least about 10 newtons per centimeter$^2$. In certain aspects, embodiments can comprise hollow nanotubular structures and the nanofibers can optionally comprise one or more associated moiety (optionally a functional moiety, e.g., one which causes a van der Waals attraction between the nanofiber and one or more of the surfaces to be greater than a van der Waals attraction between the nanofiber and such surface in the absence of the moiety.

These and other objects and features of the invention will become more fully apparent when the following detailed description is read in conjunction with the accompanying figures.

DETAILED DESCRIPTION

Figure 1:
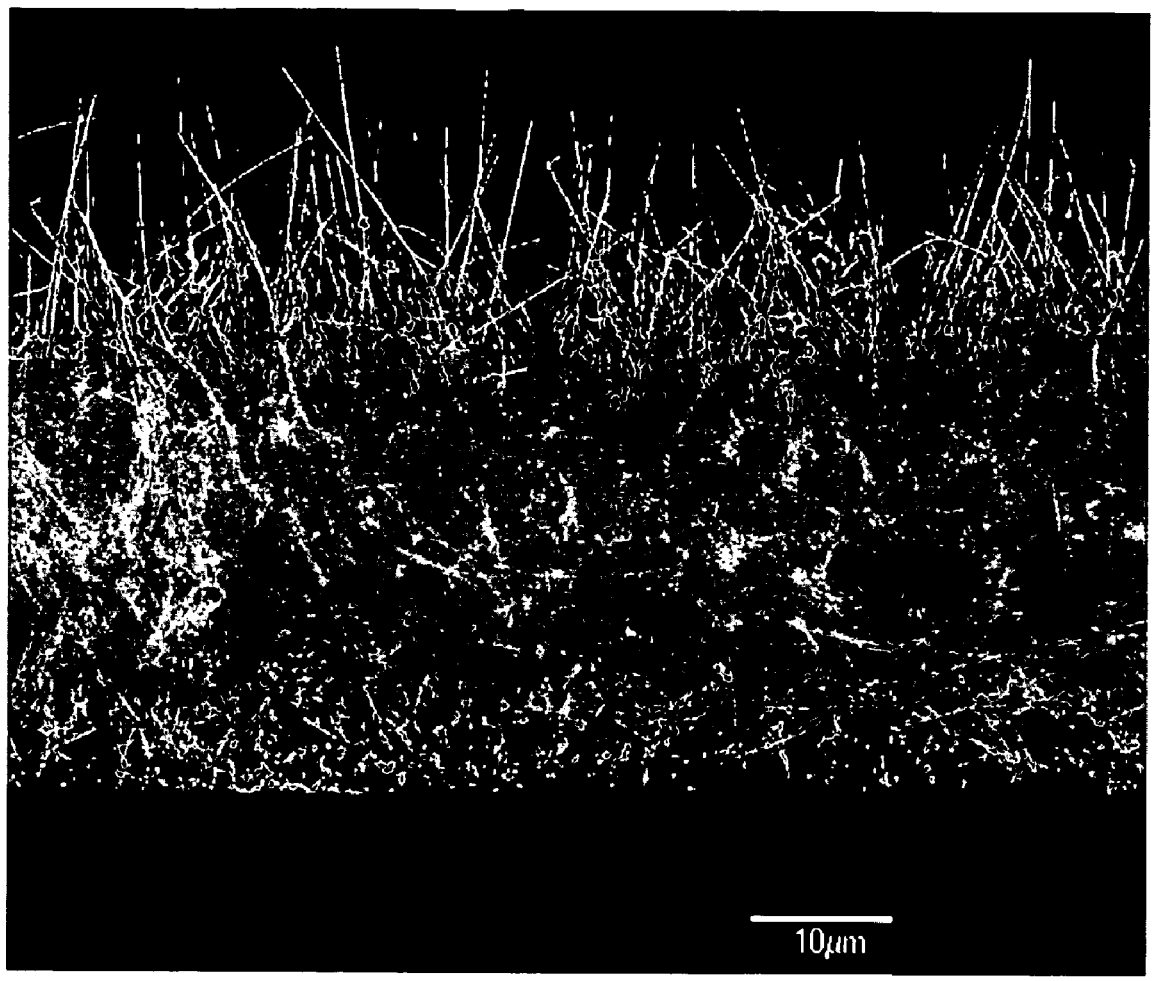
FIG. 1: Displays a photomicrograph of an exemplary adherent nanofiber structure of the invention.

As stated previously, contact adhesives are often based on soft, sticky polymers that conform to surfaces and adhere through van der Waals forces. Unfortunately, common contact adhesives are subject to a number of limitations. For example, the layer of such contact adhesive needed to adhere materials together is usually hundreds of microns to millimeters thick and such adhesives can soften with increased temperature. Such typical contact adhesives can also often leave unwanted residues on surfaces or even outgas over time.

Typical contact adhesives rely on low modulus polymers having low glass transition temperatures. Such contact adhesives, thus, can conform to surfaces on a nanometer scale and form van der Waals bonds at ambient application temperatures. However, the low modulus of the polymers often leads to poor load bearing capabilities, softening of the adhesive at elevated temperatures, and brittleness at low temperatures. Additionally, typical adhesive compounds or mixtures often include tackifiers (e.g., coumarone/indene resins, phenol/terpine resins, etc.) to increase adhesion. Unfortunately, such tackifiers are often volatile, and therefore reduce the utility of such adhesives in medical applications, aerospace applications, clean room applications and the like Other common types of adhesive compounds include, e.g., two-part reactive adhesives (such as epoxies) and solvent-based or heat-activated adhesives. These types of adhesive compounds often require at least a moderate level of skill to apply and can often release vapors until they are cured or set. The vapors released can be hazardous and/or toxic to animal/plant life or can cause decay of nearby materials such as plastics or fibers which come into contact with the vapors. If a structural or covalent bond is desired, these adhesive compounds also often require primers or coupling agents to prepare the surfaces to be bound before the liquid adhesive is applied.

Another disadvantage to common adhesive compounds is that they experience shrinkage during cure or polymerization. The shrinkage can be, e.g., up to 2-5% on epoxies, etc. Shrinkage can be extremely detrimental in many situations. For example, adhesive shrinkage can cause misalignment of surfaces and even material breakage.

The current invention comprises adherent materials and methods of adhering two or more articles, materials, or surfaces together while avoiding such problems as, e.g., thick adhesive layers, volatility, the performance restrictions of low modulus/low glass transition temperature materials, etc. The adherent materials and methods of the invention are, depending upon grammatical context and the like, also sometimes referred to herein as adhesion materials and methods, or even adhesive materials and methods. However, it will be appreciated that similarity to traditional "contact adhesives" etc. is not implied, nor should be inferred.

Without being bound to a particular theory or mechanism of operation, the concept of nanofiber adhesion of the invention is believed to operate on the principle that even high modulus materials (e.g., silicon), when present as fine enough nanofibers, will be compliant enough to allow close access between the fibers and a secondary substrate. This closeness activates van der Waals forces between the fibers and the secondary surface and so generates adhesion between the nanofibers and the secondary surface. Of course, if the nanofibers are attached (either covalently or through van der Waals forces, etc.) to a first substrate, then the first and second substrates will be adhered together. In other embodiments, it is believed that friction forces created between the high surface area between the nanofibers and an opposing surface optionally joins the surfaces together (e.g., prevents their movement relative to one another, prevents slipping, etc.) when normal force is applied. As explained in greater detail below, the nanofibers involved herein allow greater contact between surfaces than would otherwise be the case. This is because the individual fibers are rigid enough to "stand up" from one surface and touch the other surface and compliant enough to bend/give, etc. to touch the various irregularities in the other surface, thus, making greater contact than would otherwise occur. See, discussion of FIG. 3 below. This increase in intimate surface area contact (i.e., touching) between the surfaces can therefore lead to increased van der Waals forces and/or increased friction between the surfaces.

Although the current invention is described generally in terms of adhesion and joining of articles, etc., it will be appreciated that such terms, and, thus, the present invention, encompass more transient associations between surfaces, e.g., providing for enhanced gripping or friction between surfaces, that may be applied to myriad different applications including those specifically described herein.

As stated previously, some recent research in adhesion, see, e.g., K. Autumn et al., *Nature* (2000) 405:681-685, has focused on the physical surface structures of gecko feet. The gecko's foot surfaces, which in some aspects are similar to synthetic nanofibers, have been offered as an explanation for the gecko's amazing climbing ability. As shown in the Examples below, this principle (i.e., adhesion through physical surface structure rather than exuded polymers, or other similar contact adhesives, etc.) has been expanded and proven for crystalline nanofibers. See, below. As explained, the concepts and uses of the current invention are also optionally used with other materials such as carbon nanotubes and metallic nanofibers, etc. and other materials that combine the desired properties of rigidity and compliance.

The close proximity that the nanofibers achieve to the secondary surface also, in some embodiments, allows covalent bonding when the two surfaces are appropriately functionalized. See, below. Such covalent bonding previously has only been done through use of high forces and pressures and between hard surfaces (i.e., to generate the intimate contact needed) or with liquid systems. However, as explained herein, when nanofibers comprised of an appropriately rigid material, which also comprises the appropriate compliance (e.g., crystalline nanofibers) are attached to a first substrate and are contacted with a second substrate, they adhere instantly and form a structural bond. The nanofiber substrates herein can be adhered to a wide variety of secondary substrates including glass, steel and plastic, or more generally, ceramics, metals, polymers, etc., with significant adhesion. Of course, it will be appreciated that the greatly increased surface areas involved in the contact between nanofibers/surface, etc. can also allow for a stronger bond when traditional adhesive substances are applied.

In typical embodiments herein, a layer of nanofibers is provided between two or more surfaces that are to be joined or adhered. The layer of nanofibers form coupling interactions with the surfaces, thus, joining/adhering them together. Providing the nanofibers between the surfaces is optionally accomplished by providing the fibers covalently coupled to a first surface (e.g., by growing nanofibers directly on the first surface or by, e.g., separately covalently attaching the fibers to the first surface), followed by mating the fiber-covered surface with a surface of a second article or material. Additionally and/or alternatively, nanofibers are optionally deposited on one or both surfaces and permitted to associate with the initial surface by the same mechanism which is ultimately exploited to couple the second surface to the first surface (e.g., van der Waals forces or the like). Other embodiments comprise wherein nanofibers are grown on and/or deposited upon one or both sides of a flexible foil, flexible sheet, or the like which is inserted between two or more articles and, thus, form a bond between the nanofibers on the flexible foil and surfaces of the two or more articles. Other embodiments comprise nanofibers present on both surfaces of articles to be joined. One of skill in the art will readily grasp the various permutations of nanofiber placement/deposition upon various surfaces, interstices, etc. comprised within the invention In some embodiments, the invention involves contacting a first surface and at least a second surface, so that van der Waals forces cause the surfaces to adhere together. Of importance in such embodiments herein is that the first surface (and in some embodiments the second surface also) comprises a plurality of nanofibers attached to, or associated with, the surface. The presence of the nanofibers allows a much greater surface area of contact between the two surfaces and the intimate contact thus formed allows van der Waals forces to adhere the surfaces to one another and/or allows increased friction to between the surfaces (or keeps the surfaces from sliding past one another, etc.). As explained above, other embodiments herein comprise nanofibers deposited between two surfaces, etc. See, above.

In typical embodiments herein, the surfaces (i.e., the surfaces to be adhered) and the nanofibers on the surfaces (whether on one surface or on both surfaces, free nanofibers deposited between the surfaces or on a third surface between the first and second surfaces) can optionally comprise any number of materials. The actual composition of the surfaces and the nanofibers is based upon a number of possible factors. Such factors can include, for example, the intended use of the adhered surfaces, the conditions under which they will be used (e.g., temperature, pH, presence of light (e.g., UV), atmosphere, etc.), the amount of force to be exerted on the bond between the surfaces, the durability of the surfaces and the bond, cost, etc. For example, the ductility and breaking strength of nanowires will vary depending on, e.g., their composition. Thus, ceramic ZnO wires can be more brittle than silicon or glass nanowires, while carbon nanotubes may have a higher tensile strength. If the strength of the attachment of a nanowire to a substrate is lower than the van der Waals bonding strength or the friction force when a normal force is applied, such can help determine the strength required to break the adhesion.

Some possible materials used to construct the nanofibers and nanofiber surfaces herein, include, e.g., silicon, ZnO, TiO, carbon, carbon nanotubes, glass, and quartz. See, below. The nanofibers of the invention are also optionally coated or functionalized, e.g., to enhance or add specific properties. For example, polymers, ceramics or small molecules can optionally be used as coating materials for the nanofibers. The optional coatings can impart characteristics such as water resistance, improved mechanical or electrical properties or higher van der Waals forces, etc. In other words, a moiety or coating added to a nanofiber can act to increase the van der Waals attraction between such nanofiber and a substrate/surface it is to be adhered to and/or can increase friction, when a normal force is applied, between the nanofiber and a substance/surface it is to be adhered to. Additionally, in some embodiments, a moiety or coating can serve as a covalent binding site (or other binding site) between the nanofiber and a substrate/surface it is to be adhered to.

Of course, it will be appreciated that the current invention is not limited by recitation of particular nanofiber and/or substrate composition, and that any of a number of other materials are optionally used in different embodiments herein. Additionally, the materials used to comprise the nanofibers can optionally be the same as the material used to comprise the first surface and the second surface (or third surface, etc.), or they can be different from the materials used to construct the first surface or the second surface (or third surface, etc.).

In various embodiments herein, the nanofibers involved are optionally grown on a first substrate and then subsequently transferred to a second substrate which is used in the adhesion process. Such embodiments are particularly useful in situations wherein the substrate desired needs to be flexible or conforming to a particular three dimensional shape that is not readily subjected to direct application or growth of nanofibers thereon. For example, nanofibers can be grown on such rigid surfaces as, e.g., silicon wafers or other similar substrates. The nanofibers thus grown can then optionally be transferred to a flexible backing such as, e.g., rubber or the like. Again, it will be appreciated, however, that the invention is not limited to particular nanofiber or substrate compositions. For example, nanofibers are optionally gown on any of a variety of different surfaces, including, e.g., flexible foils such as aluminum or the like. Additionally, for high temperature growth processes, any metal, ceramic or other thermally stable material is optionally used as a substrate on which to grow nanofibers of the invention. Furthermore, low temperature synthesis methods such as solution phase methods can be utilized in conjunction with an even wider variety of substrates on which to grow nanofibers. For example, flexible polymer substrates and other similar substances are optionally used as substrates for nanofiber growth/attachment. See, below for a more detailed discussion and references.

In yet other embodiments herein, the nanofibers involved can optionally comprise physical conformations such as, e.g., nanotubules (e.g., hollow-cored structures), nanowires, nanowhiskers, etc. A variety of nanofibers are optionally used in this invention including carbon nanotubes, metallic nanotubes, metals and ceramics. As long as the fibers involved are concurrently rigid enough to extend above a primary surface and compliant enough (e.g., capable of molding or conforming or bending to meet or come into contact with an uneven surface, see, discussion of FIG. 3 below) to make intimate contact with the secondary surface and have the appropriate chemical functionality (whether arising innately or through addition of a moiety to the nanofiber) to generate strong enough van der Waals forces or other physical or chemical interactions to generate adhesion forces, then such nanofibers are optionally used in the invention. Thus, those of skill in the art will be familiar with similar nanostructures (e.g., nanowires and the like) which are amenable to use in the methods and devices of the invention.

In various embodiments herein, van der Waals attraction between a first surface and at least a second surface can optionally comprise greater than about 0.1 newton per centimeter$^2$ or more. Of course, such van der Waals attractions are typically (but not necessarily solely) between the nanofibers and the second surface and optionally the nanofibers and the first surface.

Additionally, in other embodiments herein, van der Waals forces between individual nanofibers on a first surface and a second surface can optionally comprise, e.g., from about 1 newton per centimeter$^2$ to about 100 newtons per centimeter$^2$ or more. In some embodiments van der Waals forces between individual nanofibers on a first surface and a second surface optionally comprise approximately 2 newtons per centimeter$^2$. Again, it will be appreciated that recitation of specific force amounts between surfaces and nanofibers, etc. should not be construed as limiting. This is especially true since the present invention encompasses myriad nanofiber and substrate compositions which can optionally affect the van der Waals and other forces between the nanofibers and/or substrates which, in turn, affect the level of adhesion involved. Furthermore, as explained below, various functionalities (either inherent to the nanofibers and/or substrates or added to the nanofibers and/or substrates) optionally act to alter the van der Waals or other attractive forces between the nanofibers and/or substrates. Thus, recitation of exemplary adherent forces (e.g., 1 newton per square centimeter, etc.) should not be taken as necessarily limiting since the invention encompasses various configurations which present any of a number of different levels of adhesion.

It is to be understood that this invention is not limited to particular configurations, which can, of course, vary (e.g., different combinations of nanofibers and substrates and optional moieties, etc. which are optionally present in a range of lengths, densities, etc.). It is also to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a nanofiber" optionally includes a plurality of such nanofibers, and the like. Unless defined otherwise, all scientific and technical terms are understood to have the same meaning as commonly used in the art to which they pertain. For the purpose of the present invention, additional specific terms are defined throughout.

Functionalization

Some embodiments of the invention comprise nanofiber and nanofiber surfaces in which the fibers include one or more functional moiety (e.g., a chemically reactive group) attached to them. Functionalized nanofibers will bring such reactive moiety into intimate contact with a surface where it can, e.g., chemically interact with that surface, either through van der Waals forces, friction, or by binding covalently with a chemical group on that surface, etc. Thus, such moieties can optionally comprise components which will form a covalent bond between the nanofiber and the surface to which it is contacted. However, in other embodiments, the moieties are optionally groups which increase the dielectric constant of the nanofiber, thus, increasing the van der Waals attraction between the nanofiber and the surface to which it is contacted. In other words, the functional moiety acts to increase the van der Waals attraction between the nanofiber and the surface to be greater than what such force would be without the moiety. Conversely, in some embodiments, such moieties can act to decrease the van der Waals attraction between the nanofiber and the surface (e.g., in uses which require a weaker bond than would otherwise result without the moiety). Also, certain moieties can optionally increase or decrease friction forces between the nanofibers and opposing surfaces when a normal force is applied. Furthermore, the moiety attached/associated with the nanofibers can be specific for another moiety on a surface to be contacted (e.g., streptavidin on either the nanofiber or the surface to be contacted, matched up with biotin on the other surface or an epoxy group matched up with an amine group on the other surface, etc.). Those of skill in the art will be familiar with numerous similar pairings which are optionally used herein (e.g., amines and boron complexes, etc.).

For example, details regarding relevant moiety and other chemistries, as well as methods for construction/use of such, can be found, e.g., in Kirk-Othmer Concise Encyclopedia of Chemical Technology (1999) Fourth Edition by Grayson et al (ed.) John Wiley & Sons, Inc, New York and in Kirk-Othmer Encyclopedia of Chemical Technology Fourth Edition (1998 and 2000) by Grayson et al (ed.) Wiley Interscience (print edition)/John Wiley & Sons, Inc. (e-format). Further relevant information can be found in *CRC Handbook of Chemistry and Physics* (2003) 83$^{rd}$ edition by CRC Press. Details on conductive and other coatings, which can also be incorporated onto nanofibers of the invention by plasma methods and the like can be found in H. S. Nalwa (ed.), *Handbook of Organic Conductive Molecules and Polymers*, John Wiley & Sons 1997. See also, U.S. Pat. No. 6,949,206 by Whiteford et al. Details regarding organic chemistry, relevant e.g., for coupling of additional moieties to a functionalized surface of nanofibers can be found, e.g., in Greene (1981) *Protective Groups in Organic Synthesis*, John Wiley and Sons, New York, as well as in Schmidt (1996) *Organic Chemistry* Mosby, St Louis, Mo., and March's *Advanced Organic Chemistry Reactions, Mechanisms and Structure*, Fifth Edition (2000) Smith and March, Wiley Interscience New York ISBN 0-471-58589-0.

Thus, again as will be appreciated, the substrates involved, the nanofibers involved (e.g., attached to, or deposited upon, the substrates) and the like can be varied. For example, the length, diameter, conformation and density of the fibers can be varied, as can the composition of the fibers and their surface chemistry.

Measurement of Adhesion

Adhesion between substrates and nanofibers is optionally measured in a number of ways. By way of example, adhesive properties may be measured by a determination of the force required to separate two coupled articles or surfaces or the force required to move/slip two joined/adhered surfaces past one another. Systems for performing such measurements include, e.g., Universal Material Test Systems available from, e.g., Instron Corp. (Canton, Mass.). Those of skill in the art will be familiar with this and other similar means of measurement of adhesion forces.

Alternatively, for rough measurements, adhesion can be measured by attaching weight (which applies a separating force) to one article or surface that is joined to another. The weight is applied and held constant, or applied in increasing amount, until separation occurs. Comparison is then made between that measurement and a set of controls. Thus, for example, shear strength measurement is optionally determined by applying a force parallel to the contacted surfaces. The dimensions of the contacted areas are optionally determined and the amount of force or weight (applied parallel to the contacted surfaces) needed to break apart the contacted areas is measured, thus, allowing calculation of the bond strength between the surfaces.

Density and Related Issues

Figure 2A:
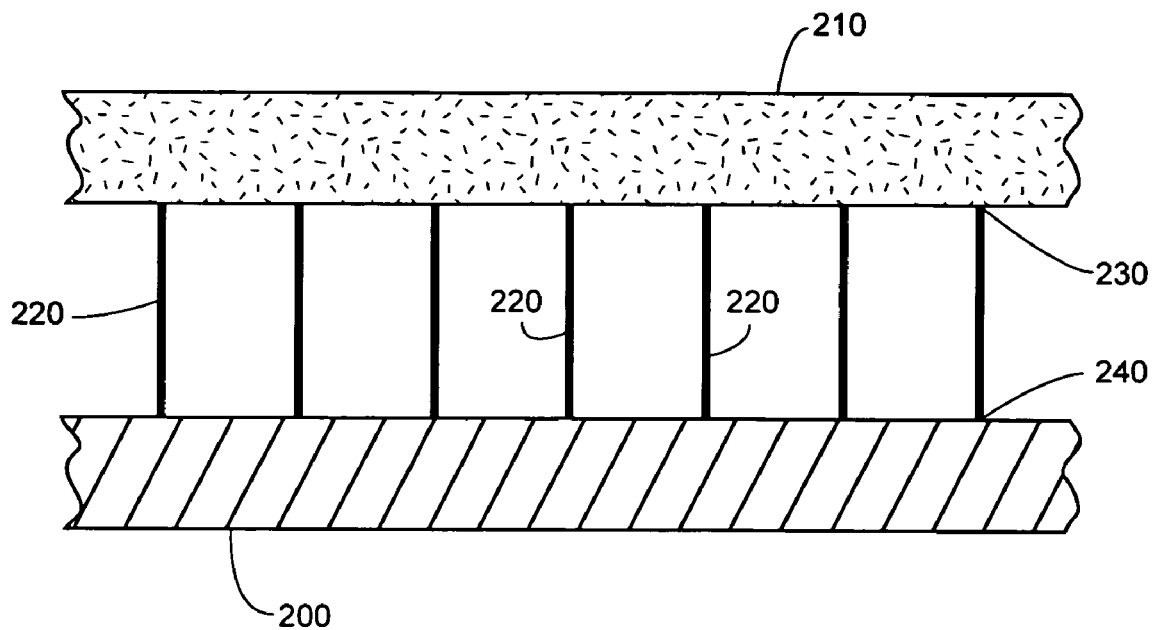
FIG. 2, Panels A and B: Schematically illustrate the contact and van der Waals attractions and/or friction forces between nanofibers and/substrate surfaces.
Figure 2B:
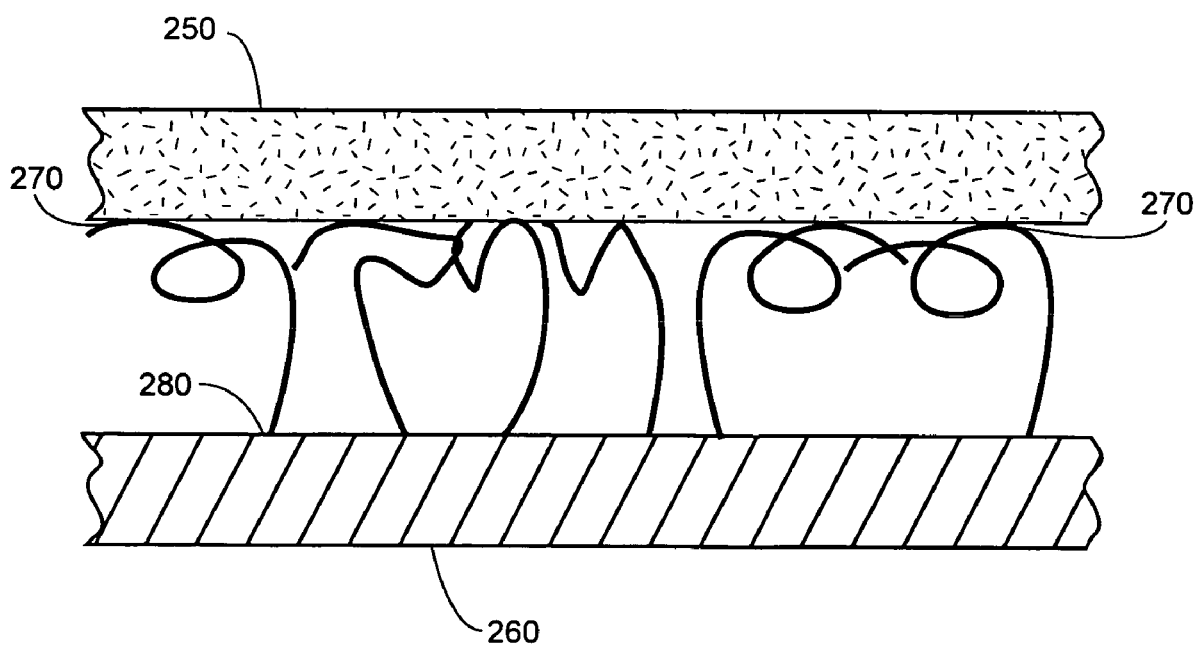

Without being bound to a particular theory of operation or mechanism of action, it is believed that the amount of intimate contact between two surfaces, e.g., the areas involved in van der Waals interactions, is directly related to the level of adhesion between the two surfaces. Further, as alluded to above, it is believed that nanoscale fiber surfaces provide enhanced levels of intimate contact relative to planar or flat surfaces (i.e., ones without nanofiber structures), by virtue of their ability to make such intimate contact between the surfaces. Such is true despite the presence of surface variations or contamination from dust, dirt or other particulates. It will thus be appreciated that "flat" surfaces (i.e., ones without nanofiber structures, etc.) really aren't flat. They have bumps, ridges, etc. which prevent true intimate contact which would create, e.g., van der Waals attractions, etc. See, e.g., FIG. 3a which illustrates a hypothetical mating of two "flat" surfaces, 300 and 310. The schematic of the surfaces shows that actual intimate contact (which would create van der Waals forces) only occurs at a few locations, 320. FIGS. 2a and 2b show that greater intimate contact occurs between surfaces when nanofibers are used as described herein, e.g., intimate contact occurs at each point, 230 or 270 where a nanofiber touches surface 210 or 250. As will be appreciated, nanofibers, 220, in FIG. 2A are depicted as straight vertical nanofibers whose contact with the surfaces occurs at their tips. FIG. 2B, however, depicts nanofibers that curve/curl, etc., and which have multiple contact points with the surfaces. In FIG. 2, the nanofibers are covalently bound to a first surface, 200 or 260, (e.g., the nanofibers are grown on such first surface) but such should not be construed as limiting on other embodiments herein. For example, as detailed herein, nanofibers can be grown on a separate surface and then transferred to the surfaces to be adhered together, etc.

Figure 3A:
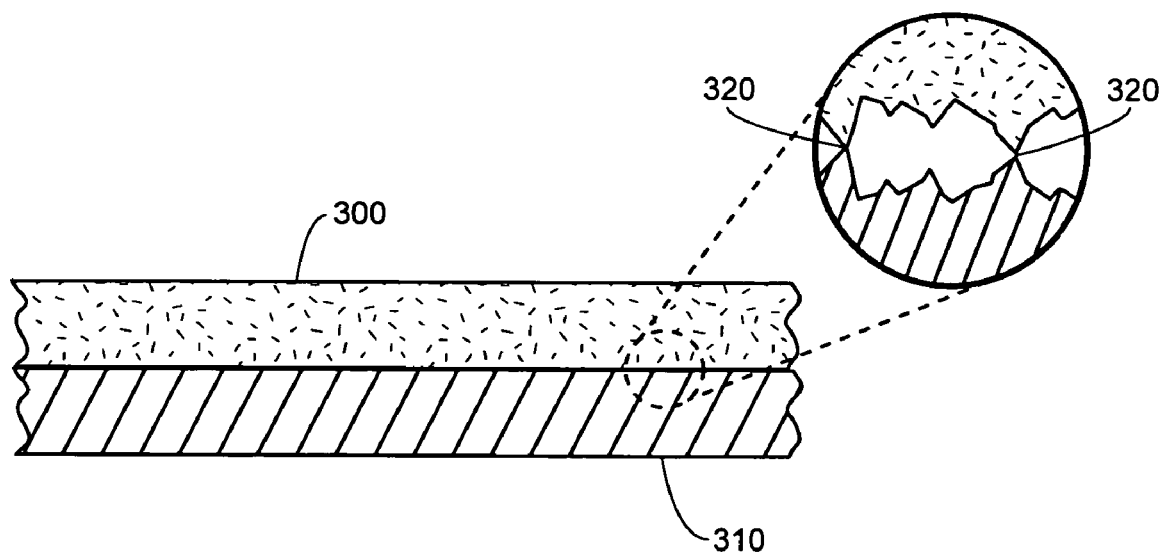
FIG. 3, Panels A, B, C and D: Schematically illustrate various concepts of intimate contact between nanofibers and substrate surfaces.
Figure 3B:
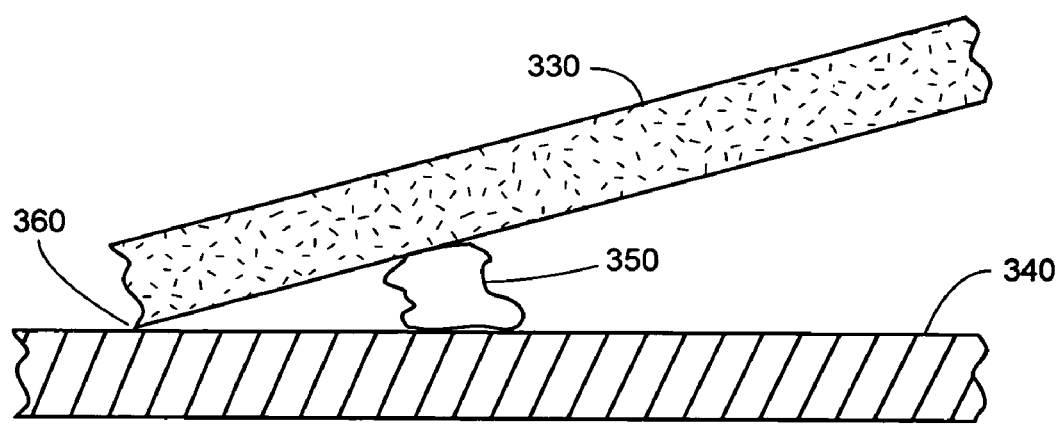
Figure 3C:
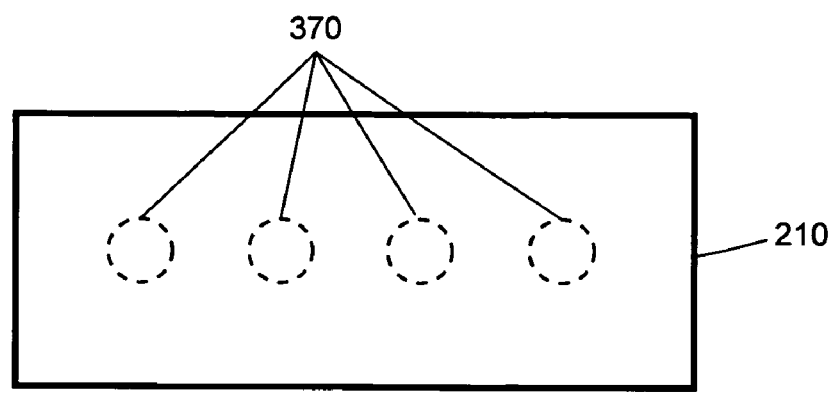
Figure 3D:
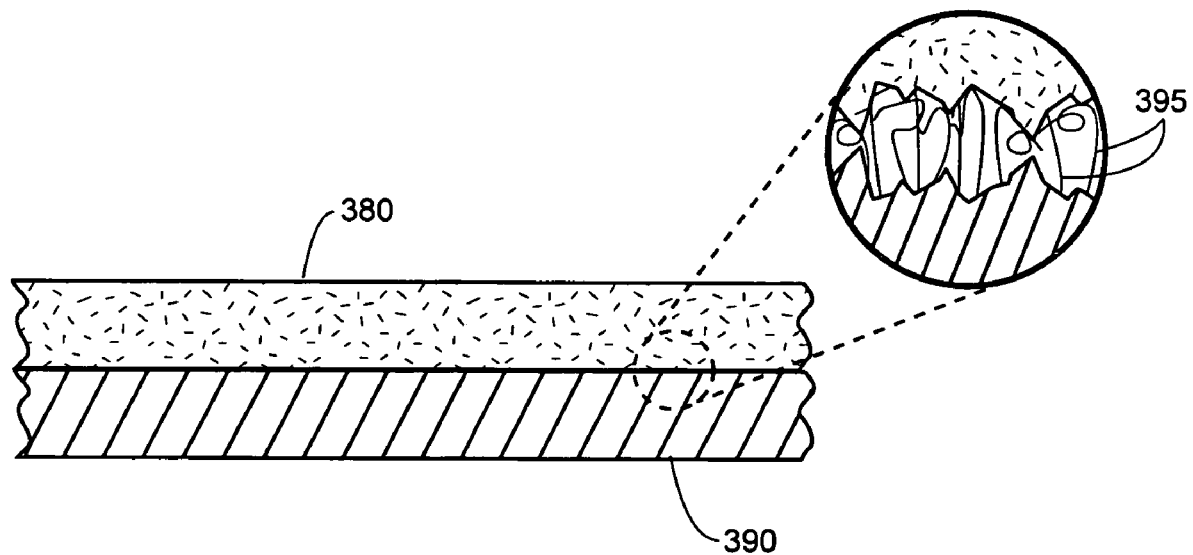

Based upon the foregoing, therefore, it is expected that the amount of intimate contact between a first substrate and a second substrate, in terms of the percentage of the overlapped surface area that is involved in such contact (also referred to herein as the "contact density" or, in some contexts, as the "percent contact" or "percent contact area"), will have a primary effect on the strength of adhesion between the two substrates. In the case of a first article that includes a nanofiber surface bound to a second planar surface, such contact density would be measured by the percentage of area of the second substrate surface that is intimately contacted by the nanofibers on the first surface. FIG. 3 schematically illustrates the measurement of contact density using two contacting planar surfaces (FIG. 3A), two planar surfaces that are not perfectly planar or between which some dust or dirt has been deposited (FIG. 3B), and a nanofiber surface and a planar surface (FIG. 3C showing a top view and FIG. 3D). As can be seen in FIG. 3A, while two planar surfaces without nanofibers, 300 and 310, may seem to be in close intimate contact, in reality, due to surface irregularities, etc., they are only in intimate contact at a few points, 320. Such few intimate contact points are typically not enough to generate large enough amounts of van der Waals forces, etc., to adhere the surfaces together. The measurement of the intimate contact in 3A, thus, could be viewed as the amount or percent of the surface area of the surface of 300 which is touched by the surface of 310, i.e., just the amount or percent which consists of contact points 320. FIG. 3D shows a similar interaction, but with a nanofiber surface of the invention. FIG. 3D schematically displays two surfaces, 380 and 390, which are similar to those in FIG. 3A (i.e., 300 and 310), except that one surface, 390 comprises nanofibers, 395, as described herein. As can be seen, the nanofibers allow much greater contact between the surfaces and, thus, generation of greater van der Waals forces, etc. The amount or percent of intimate contact area, 360, in FIG. 3B consists of just that area of contact between 330 and 340. Obstacle 350 prevents other areas of intimate contact from occurring. Of course, it will be appreciated that area 360 can also be similar to 320 in enlarged view of 3A (i.e., only small points of intimate contact within 360). FIG. 3C displays an enlarged top view of FIG. 2A. The areas of intimate contact between nanofibers 220 and surface 210 are shown as dotted circles 370 (from a top view). Thus, the amount or percent of intimate contact (i.e., contact density) would comprise the amount of area within circles 370 (and/or percent of surface area 210 occupied by circles 370). Of course, it is to be understood that FIGS. 2A, 2B, 3C and 3D, etc. are simplified for illustrative purposes and that typical embodiments can have a greater number of nanofibers, etc. See, throughout.

Also, it will be appreciated that determination of the amount of intimate contact between two substrates that are joined, e.g., by deposit of nanofibers between the surfaces can be viewed from the point of view of either surface. However, if the nanofibers are covalently joined or grown from a first surface, then the point of view of percent contact, etc. is typically viewed as exampled above. Also, for joining of surfaces that both comprise nanofiber surfaces, the amount of intimate contact can also be viewed from the point of view of either surface. Again, it will be noted that various nanofibers involved can touch one or more surface one or more times (e.g., through curving or the like) and can touch at different angles than just perpendicular (e.g., a nanofiber can have intimate contact with a surface through touching the surface along the side of the nanofiber, thus, presenting a much greater contact area than just the tip). See, e.g., FIGS. 2B and 3D.

Contact density between a nanofiber surface and another surface (also optionally comprising nanofibers),and, thus, adhesion, will generally be a function of, inter alia, a number of structural characteristics of the nanofiber surface, including the density of wires that are grown or deposited upon the first surface, the thickness of each fiber, and the length and conformation of each fiber. Regardless of the mechanism of action of the adherent surfaces described herein, the foregoing structural characteristics are expected to show enhanced adhesion between surfaces.

In terms of density, it is clear that by including more nanofibers emanating from a surface, one automatically increases the amount of surface area that is extended from the basic underlying substrate, and would thereby increase the intimate contact area with a second surface. As explained in more detail below, the embodiments herein optionally comprise a density of nanofibers on the first (and optionally second) surface of from about 1 to about 1000 or more nanofibers per micrometer$^2$ of the substrate surface. Again, here too, it will be appreciated that such density depends upon factors such as the diameter of the individual nanofibers, etc. See, below. The nanowire density influences the percent contact area (or contact density), since a greater number of nanofibers will tend to increase the percent contact area between the surfaces. As explained above, the van der Waals attraction between the adhered surfaces relies in large part upon the numerous nanofibers on at least one of the surfaces and/or between the surfaces. Such density of nanofibers on a first surface can typically correspond in a rough fashion to a density of contact points on a second surface. However, as explained throughout, nanofibers which curve, etc. and touch a surface (or even more than one surface) multiple times will act to increase the amount of intimate contact to be greater than just the number of nanofibers per unit area of the first surface. Therefore, the density of the nanofibers herein has a bearing on the adhesion of the surfaces because such density is one factor in the area of contact between the surfaces.

The percent contact between a nanofiber (or a group of nanofibers) and a second surface comprises, e.g., the percentage of the second surface, in unit area, touched, contacted, or covered by the one or more nanofiber. Thus, if a second surface consisted of 100 square microns and was touched by a nanofiber whose actual touching point consisted of 10 square microns, then the percent contact (i.e., amount of intimate contact) would be 10%. In some embodiments, herein, the invention can comprise methods and devices wherein the percent contact ranges from, e.g., about 0.01% to about 50% or greater; from about 0.1% to about 40% or greater; from about 1% to about 30% or greater; from about 2% to about 20% or greater; from about 3% to about 10% or greater; from about 4% to about 5% or greater. In some embodiments herein, the percent contact (i.e., intimate contact) optionally comprises from approximately 0.1% to approximately 5% or greater. See, FIG. 3 above.

Different embodiments of the invention comprise a range of such different densities (e.g., number of nanofibers per unit area of a substrate to which nanofibers are attached or associated). The number of nanofibers per unit area can optionally range from about 1 nanofiber per 10 micron$^2$ up to about 200 or more nanofibers per micron$^2$; from about 1 nanofiber per micron$^2$ up to about 150 or more nanofibers per micron$^2$; from about 10 nanofibers per micron$^2$ up to about 100 or more nanofibers per micron$^2$; or from about 25 nanofibers per micron$^2$ up to about 75 or more nanofibers per micron$^2$. In yet other embodiments, the density can optionally range from about 1 to 3 nanofibers per square micron to up to approximately 2,500 or more nanofibers per square micron.

In terms of individual fiber dimensions, it will be appreciated that by increasing the thickness or diameter of each individual fiber, one will again, automatically increase the area of the fiber that is able to make intimate contact with another surface, whether such contact is with a fiber that is directly orthogonal to the second surface or is parallel or tangential with that other surface. The diameter of nanofibers herein can be controlled through, e.g., choice of compositions and growth conditions of the nanofibers, addition of moieties, coatings or the like, etc. Preferred fiber thicknesses are optionally between from about 5 nanometer or less up to about 1 micron or more (e.g., 5 microns); from about 10 nanometer or less to about 750 nanometers or more; from about 25 nanometer or less to about 500 nanometers or more; from about 50 nanometer or less to about 250 nanometers or more, or from about 75 nanometer or less to about 100 nanometers or more. In some embodiments, the nanofibers comprise a diameter of approximately 40 nanometers. Choice of nanofiber thickness can also be influenced by compliance of such nanofibers (e.g., taking into account that nanofiber's composition, etc.). Thus, since some compositions can produce a less compliant nanofiber at greater diameter such changes can optionally influence the choice of nanofiber diameter.

In the case of parallel or tangential contact between fibers from one surface and a second surface, it will be appreciated that by providing fibers of varying lengths, one can enhance the amount of contact between a fiber, e.g., on an edge, and the second surface, thereby increasing adhesion. Of course, it will also be understood that for some fiber materials, increasing length may yield increasing fragility. Accordingly, preferred fiber lengths will typically be between about 2 microns or less (e.g., 0.5 microns) up to about 1 millimeter or more; from about 10 microns or less to about 500 micrometers or more; from about 25 microns or less to about 250 microns or more; or from about 50 microns or less to about 100 microns or more. Some embodiments comprise nanofibers of approximately 50 microns in length. Some embodiments herein comprise nanofibers of approximately 40 nanometer in diameter and approximately 50 microns in length.

Nanofibers herein can present a variety of aspect ratios. See, below. Thus, nanofiber diameter can comprise, e.g., from about 5 nanometers up to about 1 micron or more (e.g., 5 microns); from about 10 nanometers to about 750 nanometers or more; from about 25 nanometers to about 500 nanometers or more; from about 50 nanometers to about 250 nanometers or more, or from about 75 nanometers to about 100 nanometers or more, while the lengths of such nanofibers can comprise, e.g., from about 2 microns (e.g., 0.5 microns) up to about 1 mm or more; from about 10 microns to about 500 micrometers or more; from about 25 microns to about 250 microns or more; or from about 50 microns to about 100 microns or more Fibers that are, at least in part, elevated above the first surface are particularly preferred, e.g., where at least a portion of the fibers in the fiber surface are elevated at least 10 nanometers, or even at least 100 nanometers above the first surface, in order to provide enhanced intimate contact between the fibers and an opposing surface.

Again, without being specifically bound to a particular mechanism, the bonding or adherence between the surfaces or materials in many embodiments of the current invention is believed to be due to the bonding or adherence due to van der Waals forces between nanofibers and the surfaces or materials. Thus, the nanofibers, because of their high modulus and compliance create a greater surface area of intimate contact between the surfaces than would occur without the nanofibers. This, in turn, allows greater van der Waals forces to be generated and so adhere the surfaces together. Also, without being specifically bound to a particular mechanism, the bonding or adherence between the surfaces of materials in some embodiments of the current invention is believed to be due to increased friction forces between nanofibers and the surfaces or materials. Here again, the nanofibers, because of their rigidity and compliance, create a greater surface area of intimate contact between the surfaces than would occur without the nanofibers. This, in turn, allows or creates a greater friction force to be generated between the surfaces and so increase the force required to slide the surfaces past one another.

As explained throughout, the nanofibers involved herein can optionally be grown on surfaces (e.g., be covalently bound to such) and interact/bind with a second surface through van der Waals, friction or other forces (e.g., covalently binding in situations wherein the nanofibers are functionalized with moieties, etc.). In other situations herein, nanofibers are grown on a first substrate and transferred to, and bound to, a second substrate, e.g., covalently or through van der Waals forces, friction, etc. The second substrate is then adhered to a third substrate through van der Waals forces, or the like between the nanofibers on the second substrate and the surface of the third substrate. In yet other embodiments, nanofibers are deposited upon or between substrates and attach themselves through van der Waals, or other chemical and/or physical means to both of the surfaces, thus, adhering such surfaces together.

As seen in FIG. 1, the nanofibers optionally form a complex three-dimensional structure. The degree of such complexity depends in part upon, e.g., the length of the nanofibers, the diameter of the nanofibers, the length:diameter aspect ratio of the nanofibers, moieties (if any) attached to the nanofibers, and the growth conditions of the nanofibers, etc. The bending, interlacing, etc. of nanofibers, which help affect the degree of intimate contact with a secondary surface, and are optionally manipulated through, e.g., control of the number of nanofibers per unit area as well as through the diameter of the nanofibers, the length and the composition of the nanofibers, etc. Thus, it will be appreciated that the adhesion of the nanofiber substrates herein is optionally controlled through manipulation of these and other parameters.

It also will be appreciated that nanofibers can, in optional embodiments, curve or curl, etc., thus, presenting increased surface area for contact between the nanofibers and the substrate surfaces involved. The increased intimate contact, due to multiple touchings of a nanofiber with a second surface, increases the van der Waals attractions, or other similar forces of adhesion/interaction between the nanofiber and the second substrate. For example, a single curling nanofiber can optionally make intimate contact with a second substrate a number of times. Of course, in some optional embodiments, a nanofiber can even retouch the first surface if it curls/curves from the second surface back to the first surface. Due to possible multiple contact points (or even larger contact points, e.g., when a curved nanofiber presents a larger intimate contact area than just its tip diameter, e.g., if a side length of a nanofiber touches a substrate surface) between a single nanofiber and a second substrate/surface, the intimate contact area from curled/curved nanofibers can be greater in some instances than when the nanofibers tend not to curl or curve (i.e., and therefore typically present a "straight" aspect to the second surface). Therefore, in some, but not all, embodiments herein, the nanofibers of the invention comprise bent, curved, or even curled forms. As can be appreciated, if a single nanofiber snakes or coils over a surface (but is still just a single fiber per unit area bound to a first surface), the fiber can still provide multiple, intimate contact points, each optionally with a relatively high contact area, with a secondary surface Nanofibers and Nanofiber Construction The term "nanofiber" as used herein, refers to a nanostructure typically characterized by at least one physical dimension less than about 1000 nanometers, less than about 500 nanometers, less than about 200 nanometers, less than about 150 nanometers or 100 nanometers, less than about 50 nanometers or 25 nanometers or even less than about 10 nanometers or 5 nanometers. In many cases, the region or characteristic dimension will be along the smallest axis of the structure.

Nanofibers of this invention typically have one principle axis that is longer than the other two principle axes and, thus, have an aspect ratio greater than one, an aspect ratio of 2 or greater, an aspect ratio greater than about 10, an aspect ratio greater than about 20, or an aspect ratio greater than about 100, 200, or 500. In certain embodiments, nanofibers herein have a substantially uniform diameter. In some embodiments, the diameter shows a variance less than about 20%, less than about 10%, less than about 5%, or less than about 1% over the region of greatest variability and over a linear dimension of at least 5 nanometer, at least 10 nanometer, at least 20 nanometer, or at least 50 nanometer. Typically the diameter is evaluated away from the ends of the nanofiber (e.g. over the central 20%, 40%, 50%, or 80% of the nanofiber). In yet other embodiments, the nanofibers herein have a non-uniform diameter (i.e., they vary in diameter along their length). Also in certain embodiments, the nanofibers of this invention are substantially crystalline and/or substantially monocrystalline. The term nanofiber, can optionally include such structures as, e.g., nanowires, nanowhiskers, semi-conducting nanofibers and carbon nanotubes or nanotubules and the like. See, above.

The nanofibers of this invention can be substantially homogeneous in material properties, or in certain embodiments they are heterogeneous (e.g. nanofibers heterostructures) and can be fabricated from essentially any convenient material or materials. The nanofibers can comprise "pure" materials, substantially pure materials, doped materials and the like and can include insulators, conductors, and semi-conductors. Additionally, while some illustrative nanofibers herein are comprised of silicon, as explained above, they can be optionally comprised of any of a number of different materials.

The nanofibers herein are typically comprised of substances which posses the appropriate rigidity (e.g., to raise the nanofibers above the surface of a substrate) and compliance (e.g., to allow close enough interaction with substrate surfaces to form adherent interactions) and produce one or more desired chemical interaction (e.g., van der Waals attraction, covalent binding such as that through a moiety group, etc.). The composition of nanofibers is quite well known to those of skill in the art. As will be appreciated by such skilled persons, the nanofibers of the invention can, thus, be composed of any of a myriad of possible substances (or combinations thereof). Some embodiments herein comprise nanofibers composed of one or more organic or inorganic compound or material. Any recitation of specific nanofiber compositions herein should not be taken as limiting.

The nanofibers of the invention are optionally constructed through any of a number of different methods a number of which are referenced herein. Those of skill in the art will be familiar with diverse methods of constructing nanofibers capable of use within the methods and devices of the invention. Examples listed herein should not be taken as limiting. Thus, nanofibers constructed through means not specifically described herein, but which comprise adherent nanofibers and which fall within the parameters as set forth herein are still nanofibers of the invention and/or are used in the devices, or with the methods of the invention.

In a general sense, the nanofibers of the current invention often (but not exclusively) comprise long thin protuberances (e.g., fibers, nanowires, nanotubules, etc.) grown from a solid, optionally planar, substrate. Of course, in some embodiments herein, the fibers are detached from the substrate on which they are grown and attached to a second substrate. The second substrate need not be planar and, in fact, can comprise a myriad of three-dimensional conformations, as can the substrate on which the nanofibers were grown. In some embodiments herein, the second substrate is flexible, which, as explained in greater detail below, optionally aids in binding and release of substrates from the nanofibers.

For example, if nanofibers of the invention were grown on, e.g., a non-flexible substrate (e.g., such as some types of silicon wafers) they could be transferred from such non-flexible substrate to a flexible substrate (e.g., such as rubber or a woven layer material). Again, as will be apparent to those of skill in the art, the nanofibers herein could optionally be grown on a flexible substrate to start with, but different desired parameters may influence such decisions. A variety of methods may be employed in transferring nanofibers from a surface upon which they are fabricated to another surface. For example, nanofibers may be harvested into a liquid suspension, e.g., ethanol, which is then coated onto another surface. The same van der Waals forces, etc., exploited for adhesion of two articles via these nanofibers can optionally provide coupling of the fibers to this new surface. Subsequent mating of a surface of a second article then further exploits such forces in joining the two articles. Additionally, nanofibers from a first surface (e.g., ones grown on the first surface or which have been transferred to the first surface) can optionally be "harvested" by applying a sticky coating or material to the nanofibers and then peeling such coating/material away from the first surface. The sticky coating/material is then optionally placed against a second surface to deposit the nanofibers. Examples of sticky coatings/materials which are optionally used for such transfer include, but are not limited to, e.g., tape (e.g., 3M Scotch® tape), magnetic strips, curing adhesives (e.g., epoxies, rubber cement, etc.), etc. Such transfer materials are then optionally removed through various methods depending upon the transfer materials, etc. for example, ablation, washing, de-magnetizing and other procedures can optionally be used to remove transfer materials.

The actual nanofiber constructions of the invention are optionally complex. For example, FIG. 1 is a photomicrograph of a nanofiber construction capable of use in the current invention. As can be seen in FIG. 1, the nanofibers form a complex three-dimensional pattern. The interlacing and variable heights, curves, bends, etc. form a surface which provides many contact points between the substrates for van der Waals, friction, or other chemical/physical forces to act to adhere substrates together. Of course, in other embodiments herein, it should be apparent that the nanofibers need not be as complex as, e.g., those shown in FIG. 1. Thus, in some embodiments herein, the nanofibers are "straight" and do not tend to bend, curve, or curl. However, such straight nanofibers are still encompassed within the current invention.

As will be appreciated, the current invention is not limited by the means of construction of the nanofibers herein. For example, some of the nanofibers herein are composed of silicon. However, again, the use of silicon should not be construed as necessarily limiting. The formation of nanofibers is possible through a number of different approaches that are well known to those of skill in the art, all of which are amenable to the current invention.

Typical embodiments herein can be used with existing methods of nanostructure fabrication, as will be known by those skilled in the art, as well as methods mentioned or described herein. For example, the various methods of creating adherent nanofibers can be performed using nanofibers made by the methods mentioned or described herein or via other known methods. In other words, a variety of methods for making nanofibers and nanofiber containing structures have been described and can be adapted for use in various of the methods, systems and devices of the invention.

The nanofibers can be fabricated of essentially any convenient material (e.g., a semiconducting material, a ferroelectric material, a metal, etc.) and can comprise essentially a single material or can be heterostructures. For example, the nanofibers can comprise a semiconducting material, for example a material comprising a first element selected from group 2 or from group 12 of the periodic table and a second element selected from group 16 (e.g., ZnS, ZnO, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and like materials); a material comprising a first element selected from group 13 and a second element selected from group 15 (e.g., GaN, GaP, GaAs, GaSb, InN, InP, InAs, InSb, and like materials); a material comprising a group 14 element (Ge, Si, and like materials); a material such as PbS, PbSe, PbTe, AlS, AlP, and AlSb; or an alloy or a mixture thereof.

In some embodiments herein, the nanofibers are optionally comprised of silicon or silicon oxide. It will be understood by one of skill in the art that the term "silicon oxide" as used herein can be understood to refer to silicon at any level of oxidation. Thus, the term silicon oxide can refer to the chemical structure $SiO_x$, wherein x is between 0 and 2 inclusive. In other embodiments, the nanofibers can comprise, e.g., silicon, glass, quartz, plastic, metal, polymers, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, $SiO_1$, $SiO_2$, silicon carbide, silicon nitride, polyacrylonitrile (PAN), polyetherketone, polyimide, aromatic polymers, or aliphatic polymers.

It will be appreciated that in some embodiments, the nanofibers can comprise the same material as one or more substrate surface, while in other embodiments, the nanofibers do not comprise the same material as the substrates. Additionally, the substrate surfaces can optionally comprise any one or more of the same materials or types of materials as do the nanofibers (e.g., such as the materials illustrated herein).

Some, but by no means all, embodiments herein comprise silicon nanofibers. Common methods for making silicon nanofibers (e.g., which can be used with the method/devices herein) include vapor liquid solid growth (VLS), laser ablation (laser catalytic growth) and thermal evaporation. See, for example, Morales et al. (1998) "A Laser Ablation Method for the Synthesis of Crystalline Semiconductor Nanowires" Science 279, 208-211 (1998). In one example approach, a hybrid pulsed laser ablation/chemical vapor deposition (PLA-CVD) process for the synthesis of semiconductor nanofibers with longitudinally ordered heterostructures is used. See, Wu et al. (2002) "Block-by-Block Growth of Single-Crystalline Si/SiGe Superlattice Nanowires," Nano Letters Vol. 0, No. 0.

In general, several methods of making nanofibers have been described and can be applied in the methods, systems and devices herein. In addition to Morales et al. and Wu et al. (above), see, for example, Lieber et al. (2001) "Carbide Nanomaterials" U.S. Pat. No. 6,190,634 B1; Lieber et al. (2000) "Nanometer Scale Microscopy Probes" U.S. Pat. No. 6,159,742; Lieber et al. (2000) "Method of Producing Metal Oxide Nanorods" U.S. Pat. No. 6,036,774; Lieber et al. (1999) "Metal Oxide Nanorods" U.S. Pat. No. 5,897,945; Lieber et al. (1999) "Preparation of Carbide Nanorods" U.S. Pat. No. 5,997,832; Lieber et al. (1998) "Covalent Carbon Nitride Material Comprising $C_2N$ and Formation Method" U.S. Pat. No. 5,840,435; Thess, et al. (1996) "Crystalline Ropes of Metallic Carbon Nanotubes" Science 273, 483-486; Lieber et al. (1993) "Method of Making a Superconducting Fullerene Composition By Reacting a Fullerene with an Alloy Containing Alkali Metal" U.S. Pat. No. 5,196,396; and Lieber et al. (1993) "Machining Oxide Thin Films with an Atomic Force Microscope: Pattern and Object Formation on the Nanometer Scale" U.S. Pat. No. 5,252,835. Recently, one dimensional semiconductor heterostructure nanocrystals, have been described. See, e.g., Bjork et al.

(2002) "One-dimensional Steeplechase for Electrons Realized" *Nano Letters* Vol. 0, No. 0.

It should be noted that some references herein, while not specific to nanofibers, are optionally still applicable to the invention. For example, background issues of construction conditions and the like are applicable between nanofibers and other nanostructures (e.g., nanocrystals, etc.).

In another approach which is optionally used to construct nanofibers of the invention, synthetic procedures to prepare individual nanofibers on surfaces and in bulk are described, for example, by Kong, et al. (1998) "Synthesis of Individual Single-Walled Carbon Nanotubes on Patterned Silicon Wafers," *Nature* 395, 878-881, and Kong, et al. (1998) "Chemical Vapor Deposition of Methane for Single-Walled Carbon Nanotubes" *Chem. Phys. Lett.* 292, 567-574.

In yet another approach, substrates and self assembling monolayer (SAM) forming materials can be used, e.g., along with microcontact printing techniques to make nanofibers, such as those described by Schon, Meng, and Bao, "Self-assembled monolayer organic field-effect transistors," *Nature* 413:713 (2001); Zhou et al. (1997) "Nanoscale Metal/Self-Assembled Monolayer/Metal Heterostructures," *Applied Physics Letters* 71:611; and WO 96/29629 (Whitesides, et al., published Jun. 26, 1996).

Synthesis of nanostructures, e.g., nanocrystals, of various composition is described in, e.g., Peng et al. (2000) "Shape control of CdSe nanocrystals" *Nature* 404:59-61; Puntes et al. (2001) "Colloidal nanocrystal shape and size control: The case of cobalt" *Science* 291:2115-2117; U.S. Pat. No. 6,306,736 to Alivisatos et al. (Oct. 23, 2001) entitled "Process for forming shaped group III-V semiconductor nanocrystals, and product formed using process"; U.S. Pat. No. 6,225,198 to Alivisatos et al. (May 1, 2001) entitled "Process for forming shaped group II-VI semiconductor nanocrystals, and product formed using process"; U.S. Pat. No. 5,505,928 to Alivisatos et al. (Apr. 9, 1996) entitled "Preparation of III-V semiconductor nanocrystals"; U.S. Pat. No. 5,751,018 to Alivisatos et al. (May 12, 1998) entitled "Semiconductor nanocrystals covalently bound to solid inorganic surfaces using self-assembled monolayers"; U.S. Pat. No. 6,048,616 to Gallagher et al. (Apr. 11, 2000) entitled "Encapsulated quantum sized doped semiconductor particles and method of manufacturing same"; and U.S. Pat. No. 5,990,479 to Weiss et al. (Nov. 23, 1999) entitled "Organo luminescent semiconductor nanocrystal probes for biological applications and process for making and using such probes."

Growth of nanofibers, such as nanowires, having various aspect ratios, including nanofibers with controlled diameters which can be utilized herein, is described in, e.g., Gudiksen et al (2000) "Diameter-selective synthesis of semiconductor nanowires" *J. Am. Chem. Soc.* 122:8801-8802; Cui et al. (2001) "Diameter-controlled synthesis of single-crystal silicon nanowires" *Appl. Phys. Lett.* 78:2214-2216; Gudiksen et al. (2001) "Synthetic control of the diameter and length of single crystal semiconductor nanowires" *J. Phys. Chem. B* 105:4062-4064; Morales et al. (1998) "A laser ablation method for the synthesis of crystalline semiconductor nanowires" *Science* 279:208-211; Duan et al. (2000) "General synthesis of compound semiconductor nanowires" *Adv. Mater.* 12:298-302; Cui et al. (2000) "Doping and electrical transport in silicon nanowires" J. *Phys. Chem. B* 104:5213-5216; Peng et al. (2000), supra; Puntes et al. (2001), supra; U.S. Pat. No. 6,225,198 to Alivisatos et al., supra; U.S. Pat. No. 6,036,774 to Lieber et al. (Mar. 14, 2000) entitled "Method of producing metal oxide nanorods"; U.S. Pat. No. 5,897,945 to Lieber et al. (Apr. 27, 1999) entitled "Metal oxide nanorods"; U.S. Pat. No. 5,997,832 to Lieber et al. (Dec. 7, 1999) "Preparation of carbide nanorods"; Urbau et al. (2002) "Synthesis of single-crystalline perovskite nanowires composed of barium titanate and strontium titanate" *J. Am. Chem. Soc.,* 124, 1186; Yun et al. (2002) "Ferroelectric Properties of Individual Barium Titanate Nanowires Investigated by Scanned Probe Microscopy" *Nano Letters* 2, 447; and published PCT application nos. WO 02/17362, and WO 02/080280.

Growth of branched nanofibers (e.g., nanotetrapods, tripods, bipods, and branched tetrapods) is described in, e.g., Jun et al. (2001) "Controlled synthesis of multi-armed CdS nanorod architectures using monosurfactant system" *J. Am. Chem. Soc.* 123:5150-5151; and Manna et al. (2000) "Synthesis of Soluble and Processable Rod-, Arrow-, Teardrop-, and Tetrapod-Shaped CdSe Nanocrystals" *J. Am. Chem. Soc.* 122:12700-12706. Synthesis of nanoparticles is described in, e.g., U.S. Pat. No. 5,690,807 to Clark Jr. et al. (Nov. 25, 1997) entitled "Method for producing semiconductor particles"; U.S. Pat. No. 6,136,156 to El-Shall, et al. (Oct. 24, 2000) entitled "Nanoparticles of silicon oxide alloys"; U.S. Pat. No. 6,413,489 to Ying et al. (Jul. 2, 2002) entitled "Synthesis of nanometer-sized particles by reverse micelle mediated techniques"; and Liu et al. (2001) "Sol-Gel Synthesis of Free-Standing Ferroelectric Lead Zirconate Titanate Nanoparticles" *J. Am. Chem. Soc.* 123:4344. Synthesis of nanoparticles is also described in the above citations for growth of nanocrystals, nanowires, and branched nanowires.

Synthesis of core-shell nanofibers, e.g., nanostructure heterostructures, is described in, e.g., Peng et al. (1997) "Epitaxial growth of highly luminescent CdSe/CdS core/shell nanocrystals with photostability and electronic accessibility" *J. Am. Chem. Soc.* 119:7019-7029; Dabbousi et al. (1997) "(CdSe)ZnS core-shell quantum dots: Synthesis and characterization of a size series of highly luminescent nanocrystallites" *J. Phys. Chem. B* 101:9463-9475; Manna et al. (2002) "Epitaxial growth and photochemical annealing of graded CdS/ZnS shells on colloidal CdSe nanorods" *J. Am. Chem. Soc.* 124:7136-7145; and Cao et al. (2000) "Growth and properties of semiconductor core/shell nanocrystals with InAs cores" *J. Am. Chem. Soc.* 122:9692-9702. Similar approaches can be applied to growth of other core-shell nanostructures. See, for example, U.S. Pat. No. 6,207,229 (Mar. 27, 2001) and U.S. Pat. No. 6,322,901 (Nov. 27, 2001) to Bawendi et al. entitled "Highly luminescent color-selective materials."

Growth of homogeneous populations of nanofibers, including nanofibers heterostructures in which the different materials are distributed at different locations along the long axis of the nanofibers is described in, e.g., published PCT application nos. WO 02/17362, and WO 02/080280; Gudiksen et al. (2002) "Growth of nanowire superlattice structures for nanoscale photonics and electronics" *Nature* 415:617-620; Bjork et al. (2002) "One-dimensional steeplechase for electrons realized" *Nano Letters* 2:86-90; Wu et al. (2002) "Block-by-block growth of single-crystalline Si/SiGe superlattice nanowires" *Nano Letters* 2, 83-86; and US Patent Publication 2004/0026684 to Empedocles entitled "Nanowire heterostructures for encoding information." Similar approaches can be applied to growth of other heterostructures and applied to the various methods and systems herein.

The present invention can be used with structures that may fall outside of the size range of typical nanostructures. For example, Haraguchi et al. (U.S. Pat. No. 5,332,910) describe nanowhiskers which are optionally used herein. Semi-conductor whiskers are also described by Haraguchi et al. (1994) "Polarization Dependence of Light Emitted from GaAs p-n junctions in quantum wire crystals" *J. Appl. Phys.* 75(8): 4220-4225; Hiruma et al. (1993) "GaAs Free Standing Quantum Sized Wires," *J. Appl. Phys.* 74(5):3162-3171; Haraguchi et al. (1996) "Self Organized Fabrication of Planar GaAs Nanowhisker Arrays, and Yazawa (1993) "Semiconductor Nanowhiskers" *Adv. Mater.* 5(78):577-579.

Such nanowhiskers are optionally nanofibers of the invention. While the above references (and other references herein) are optionally useful for construction and determination of parameters of nanofibers for the invention, those of skill in the art will be familiar with other methods of nanofiber construction/design, etc. which can also be amenable to the methods and devices herein.

Exemplary Uses of Adhesive Nanofibers

The constructs and methods of the current invention are widely applicable to a broad range of uses, and therefore, specific mention of uses herein should not be taken as limiting. In general, the invention is useful to adhere two or more surfaces together and/or prevent or inhibit two or more surfaces from sliding past one another (i.e., typically when a normal force is applied). The invention is especially useful (but is not limited to) situations/conditions that are not conducive to use of more conventional adhesives. For example, many common adhesives are not useful under conditions such as high temperature, low temperature, high or low humidity, vacuum, or other similar conditions which can adversely effect the polymer, resin, etc. used as the adhesive. Furthermore, in certain medical uses such as attachment of medical devices in vivo or attachment of medical devices such as metal plates, etc. to bone or teeth, the adhesive used must be non-immunogenic, etc. For further examples of uses of nanofiber surfaces, e.g., in medical applications, etc., see, e.g., WO 2004/099068 and US Patent Publication 20050181195, all of which are incorporated herein in their entirety for all purposes.

The adherent nanofibers/structures of the invention and the methods of their use can easily be tailored to avoid the problems concerning ambient conditions and medical concerns (see, above) through manipulation of the parameters herein, e.g., choice of nanofiber composition material and the like. Additionally, the nature of the invention inherently avoids many of the previously mentioned typical problems (and others as well) since the adherent properties of the invention do not rely on extraneous polymers and the like which can break down or creep under extreme conditions. Instead, the current invention optionally relies upon the van der Waals attraction and/or friction between the nanofiber structures and surfaces. Therefore temperature fluctuations and the like do not alter the basic adherent bonds of the invention.

In some embodiments, the invention can be used to construct climbing or hanging equipment. For example, similar to geckos, the adherent nanostructures herein can optionally be attached to equipment (e.g., gloves, handheld pads and the like), to allow easy grip of surfaces such as walls, ceilings, rock faces, etc. The ability of the invention to be incorporated into flexible forms allows the rocking or peeling away of the nanofibers from the surface to which they are adhered. The rocking/peeling changes the contact angle of individual nanofibers in relation to the surface they are adhered to and, thus, can cause release of the individual fiber. Such release is, of course, quite useful in typical applications, e.g., in climbing, etc. Conversely, when release is not desired, the contact angle of the nanofibers is optionally not changed and so no release occurs. Such release can also optionally occur with devices/methods of the invention which comprise nanofiber surfaces that are not flexible as well. In such cases, release can be achieved by changing the contact angle, etc. of nanofibers. For example, in a clamping device or the like which incorporates nanofiber adhesion aspects of the invention, release can optionally be done by applying greater separating pressure at one contact area which creates a separating force in that area which is greater than the forces adhering the nanofibers/surfaces in that area. This could be done by, e.g., a fulcrum/scissoring motion as is commonly used in scissors/hemostats, etc. which have an X or V shaped body or the like. Thus, the remaining adhering nanofibers would then be under greater separating forces because they would be carrying a greater load (i.e., because other nanofibers were no longer in contact with the opposing surface, etc.) and could therefore be separated in a similar manner. Another point optionally involved in release is that the change in contact angle of the nanofibers between the surfaces can go from, e.g., nanofibers which present their sides to a surface (thus, creating greater intimate contact and greater adherent force) to, e.g., nanofibers which present less of their sides or just their tips to a surface (thus, creating a lower amount of intimate contact and a lower amount of adherent force). Also, in some situations involving frictional adherence, a change in applied pressure (e.g., from lateral to perpendicular to a surface) or a removal or reduction of normal force, can optionally cause release of adhered surfaces.

Yet other possible embodiments of the current invention include "setting" or "fixing" of devices/materials into place. For example, a screw put into a material (e.g., a metal plate) could be made much more stable and less prone to release by incorporating nanofiber adherents of the invention. Such incorporation could optionally be done by having nanofibers on one or more of the screw or the screw-hole which receives the screw. Also, nanofibers could optionally be placed between the screw and the screw-hole, e.g., via a slurry of nanofibers or the like. See, above. Addition of nanofibers to one or more surface, or addition of slurries or dry mixes of nanofibers, etc. could, thus, be similarly used to adhere any number of materials (e.g., screw, nails, fasteners, interlocking devices/plates, etc.).

In yet other embodiments, the methods and devices of the invention can be utilized in, e.g., aerospace applications, medical applications, or industrial processing applications where creation of bonds which are strong at an appropriate temperature, which produce little or no outgassing and which have the potential for reuse is desired.

In yet other types of embodiments, the devices and methods of the invention can optionally be used in applications wherein a normal force is applied to the substrate surfaces involved, in order to produce adherence of the substrates. Thus, in some contexts herein, "adherence," "adhesion," or the like can refer to prevention or inhibition of lateral or shear movement (e.g., slipping, sliding, or the like between surfaces such as would occur between a medical clamp and a tissue, between two tissues, etc.). Such embodiments can optionally differ from previously described embodiments in that they require application of a normal force in order to, or to help to, adhere the surfaces. However, because of the nanofiber surfaces herein, friction forces, etc. are believed to produce adherence at lower levels of normal force. Thus, such applications are especially useful in situations requiring adherence (again, here meaning prevention/inhibition of lateral movement, e.g., slipping, of surfaces), but which also require a delicate or gentle normal force. In other words, devices/methods of the invention can be used to prevent/inhibit slippage, but with application of much less normal force than would otherwise be required with non-nanofiber systems.

Therefore, devices and methods of the invention are optionally used in construction of clamps, such as those used in medical devices, hemostats or the like. Currently jaw inserts of medical clamps are typically made of rubber or metal. Rubber is usually the less intrusive option because it provides compliance (e.g., yielding or conforming to shapes due to, e.g., force applied). The addition of serrated areas or protrusions are often used to increase localized forces on the tissue being clamped. Such features are especially used for irregular surfaces such as arteries or tissue. However, the pressure applied (i.e., normal force) to effectively close off an artery or hold tissue, etc., while keeping the tissue, etc. within the clamp, can possibly damage the tissue/artery/etc. involved. Thus, it is desirable to minimize the pressure applied, but still produce the specific result, e.g., holding a tissue, clamping an artery, etc.

Figure 4:
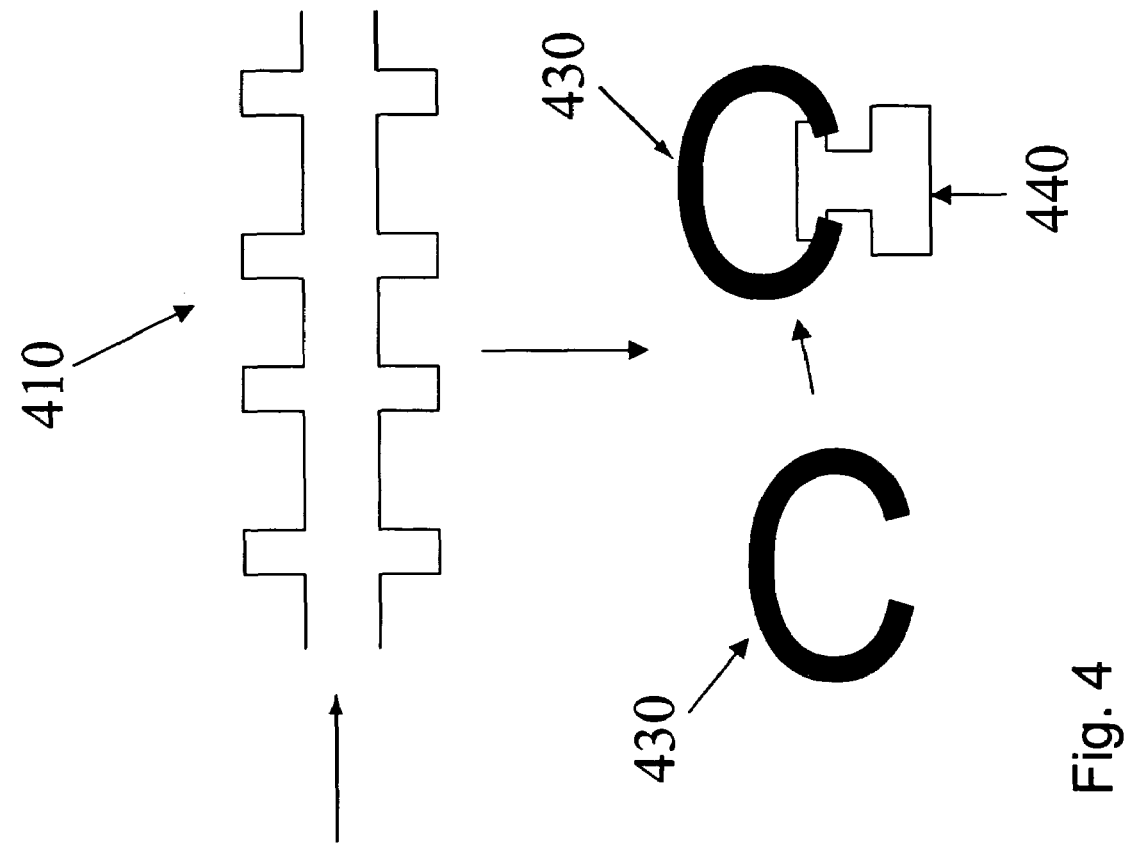
FIG. 4: Schematically illustrates construction and design of an exemplary embodiment of the invention.
Figure 4:
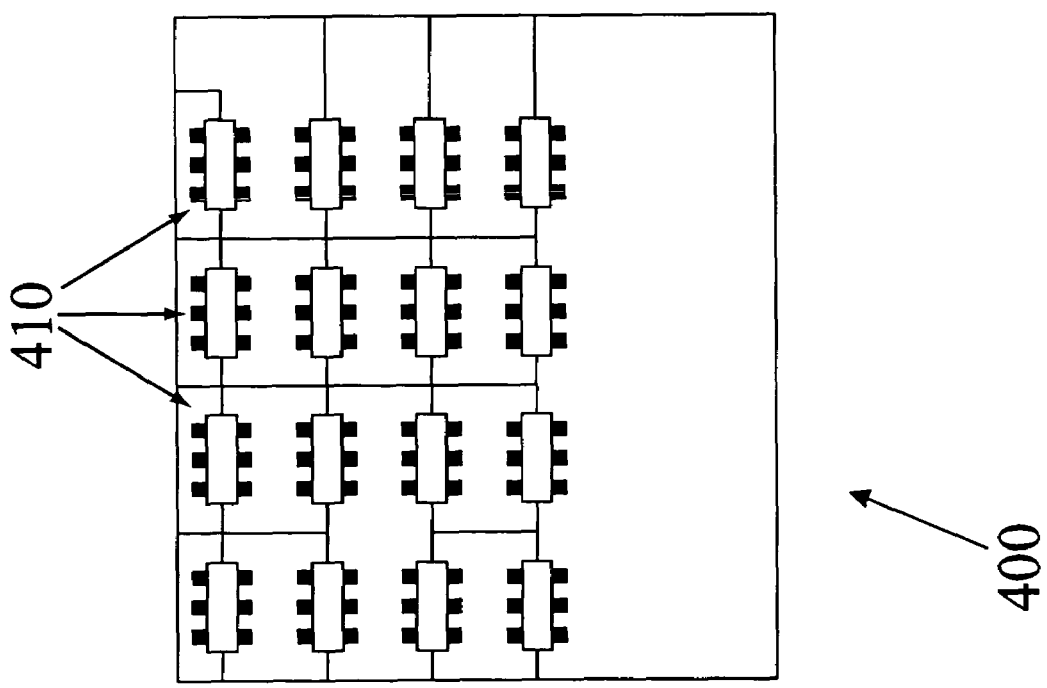

Optimization of such pressures, etc. can optionally be achieved by incorporation of nanofiber inserts in medical clamps and the like. Thin metal sheets (e.g., approximately 10 to 150 um and preferably 25-100 um) which are quite flexible and resistant to permanent deformation can be used for construction of nanofiber adhesive surfaces for the clamps. Additionally such thin metal sheets are ideal growth surfaces for nanofibers due to their high temperature resistance. For example, stainless steel, titanium, nickel, beryllium copper and nickel would all be candidate materials for construction of various medical devices incorporating aspects of the invention. Such thin films can be etched or stamped into precise and intricate shapes. See, FIG. 4 which gives schematics for one possible type of medical clamp. It will be appreciated that numerous other clamp designs and formations (incorporating the concepts of the current invention) are also possible and that the illustration in FIG. 4 should not be taken as limiting. Secondary operations are typically done to bend and form parts of clamps into three-dimensional shapes. For a clamp insert with nanofiber adherent areas, flat parts can optionally be etched or stamped and a secondary operation can optionally be performed by bending the strip into a C shape to make it into a channel to slide into the clamp as well as using the C shape to create spring forces. Such secondary operations can also optionally stamp or create serrations or protrusions on the clamp. Areas that require nanofibers can then optionally be gold plated for growth of nanofibers. Thus, for example in FIG. 4, a sheet of thin metal, 400, can be stamped or etched to produce various subparts, 410, that can be formed into devices such as clamps. Once removed from the metal sheet, the stamped or etched parts, 410 can be manipulated in various manners, e.g., bent to the proper conformation, 430 (which shows an end view), and nanofibers can be grown or deposited upon the correct face/aspect of the part (e.g., nanofibers can be grown after gold-plating, etc.). The properly manipulated part (comprising nanofibers) can then be assembled with other device parts, e.g., a clamp insert, etc., 440, to produce the device. As will be appreciated, however, numerous methods exist for creation of nanofibers for use herein (see, above) not all of which require gold plating, etc. Stamping and bending operations as would be used to create such devices are usually quite inexpensive and can result in precise high quality parts. The spring qualities and high temperature resistance of thin metals can optionally enhance the functionality of the friction characteristics of the nanofiber devices. Again, however, it will be appreciated that the nanofiber adhesive surfaces of the invention with their frictional forces will require less clamping force (i.e., normal force) on tissues, etc, and will subsequently induce less tissue damage. The forces (e.g., friction, etc.) can prevent sliding or slipping of medical devices, such as clamps, off of tissues, arteries, etc. which are typically coated with blood/bodily fluids that can cause slipping of ordinary clamps, etc.

Additionally, it will also be appreciated that such clamps and the like are optionally used in other areas besides medical settings (e.g., clamping of wires or of tubes in mechanical or industrial applications, etc), but which also would benefit from stable more gentle clamping than occurs with traditional means. Those of skill in the art will be aware of numerous other possible uses for such devices. Those of skill in the art will also be aware of many applications where the nanofiber adherent devices can hold slippery and/or hard to grasp objects (e.g., arteries, tissue, wet tubes, etc.) with a gentle grasp as opposed to a harsh clamping (e.g., harsh because of high pressure and/or sharp ridges or points or the like), which is required with other current devices, to overcome slipperiness issues and provide a firm hold.

Kits/Systems

In some embodiments, the invention provides kits for practice of the methods described herein and which optionally comprise the substrates of the invention. In various embodiments, such kits comprise a container or containers with, e.g., one or more adhesion substrate as described herein, one or more device comprising an adhesion nanofiber substrate, etc.

The kit can also comprise any necessary reagents, devices, apparatus, and materials additionally used to fabricate and/or use an adhesion nanofiber substrate, device or the like.

In addition, the kits can optionally include instructional materials containing directions (i.e., protocols) for the synthesis of adhesion nanofibers and/or adding of moieties to adhesion nanofibers and/or use of adhesion nanofiber structures and/or devices. Preferred instructional materials give protocols for utilizing the kit contents (e.g., to use the adhesion nanofibers or adhesion nanofiber methods of the invention). Instructional materials can include written material (e.g., in the form of printed material, material stored on CD, computer diskette, DVD, or the like) as well as access to an internet site which contains the appropriate instructions.

In certain embodiments, the instructional materials teach the use of the nanofiber substrates of the invention in the construction of one or more devices (such as, e.g., sealing devices, attachment devices, medical devices, etc.).

EXAMPLES

Example 1

Construction of an Adherent Nanofiber Substrate

Silicon nanofibers of approximately 40 nanometer in diameter and 50 um in length were grown on a four inch silicon wafer through a standard CVD process using gold colloids (see, e.g., above). The fiber density was approximately 2 nanofibers per square micron. To test the adhesion ability of the silicon nanofiber wafer, a microscope slide was suspended in a vertical orientation above a lab bench. A 2 centimeter×1 centimeter piece from the above silicon wafer containing the nanofibers was lightly pressed against the glass slide (with the nanofiber surface touching the glass slide). Thus, the top centimeter of the nanofiber wafer was exposed to the glass while the other centimeter was not in contact with the glass. A 200 gram weight was then attached to the free end of the silicon wafer via a binder clip. The weight was allowed to hang freely, thus, exerting a stress of 2 newtons on the nanofiber/glass interface. There was no measurable movement in the nanofiber joint in 10 days.

Example 2

Construction of an Adherent Nanofiber Substrate

Silicon nanofibers of approximately 40 nanometer in diameter and 50 um in length were grown on a 4 inch silicon wafer by the standard CVD process using gold colloids. See, e.g., above. The fiber density was approximately 2 nanofibers per square micron. To test the adhesion ability of the silicon nanofiber wafer to itself, two 2×1 centimeter pieces were cut from the silicon wafer containing the nanofibers. One centimeter of the fiber surface of each piece was lightly pressed together. One free end of the pressed pieces was clamped in a vice on a ring stand and a 100 gram weight was hung from the opposite end. The weight was allowed to hang freely, thus, exerting a stress of 1 newton on the nanofiber surface/nanofiber surface interface. There was no measurable movement in the nanofiber joints in 10 days.

Example 3

Reuse of Adherent Nanofiber Substrates

The nanofiber substrate in Example 1 was pulled away from the glass in a perpendicular direction. It was then pressed against a second suspended piece of glass and through a similar process was shown to again hold 2 newtons of force.

Example 4

Reuse of Adherent Nanofiber Substrates

A nanofiber substrate prepared as explained in Example 1 was pressed against a variety of substrates including stainless steel, Formica, painted metal and Teflon®. The substrate exhibited enough adherent force to support its own weight for all of the materials except Teflon® of which it slipped off.

Example 5

Coefficient of Friction of Adherent Nanofiber Substrates

A Micro Scratch Tester (Micro Photonics, Torrance, Calif.) was used to determine the difference in coefficient of friction between a nanofiber surface of the invention and a similar surface without nanofibers. A glass surface (i.e., a borosilicate glass microscope slide) that was chemically similar to silicon dioxide nanowires (i.e., one possible type/construction of nanofibers of the invention) was tested against a nanofiber surface similar to those used in previous example, supra. The nanofiber surface had a coefficient of friction of 2.0 while the glass slide (without nanofibers) had a coefficient of friction of 0.08.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of joining two or more articles, the method comprising:
   i) depositing a first plurality of inorganic nanofibers on a first surface of a first article, wherein the plurality of nanofibers have a curved or curled configuration;
   ii) contacting the first surface of the first article with a second surface of a second article, whereby each nanofiber contacts the second surface of the second article at a plurality of contact points wherein the contacting creates van der Waals forces between each of said nanofibers and the second surface of the second article, such that the van der Waals forces between the nanofibers and the second surface of the second article are sufficient to adhere the first and second articles together.

2. The method of claim 1, wherein said depositing comprises growing the nanofibers on the first surface of the first article.

3. The method of claim 2, wherein the nanofibers are grown by a VLS growth process.

4. The method of claim 1, wherein the nanofibers have a length of at least about 50 microns.

5. The method of claim 1, wherein the nanofibers comprise silicon or silicon oxide nanofibers.

6. The method of claim 1, wherein the nanofibers are selected from a material comprising a first element selected from group 2 or from group 12 of the periodic table and a second element selected from group 16, a material comprising a first element selected from group 13 and a second element selected from group 15, a material comprising a group 14 element, a material comprising PbS, PbSe, PbTe, AlS, AlP and AlSb, or an alloy or a mixture thereof.

7. The method of claim 1, wherein the nanofibers comprise TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, SiO1, SiO2, silicon carbide, silicon nitride, or silicon.

8. The method of claim 1, wherein the nanofibers are grown on a second article, and then transferred and deposited on the first surface of the first article.

9. The method of claim 1, wherein the density of contact points between the nanofibers and the second surface of the second article comprises contact of from at least about 1 nanofiber per micron$^2$ to 2000 nanofibers per micron$^2$.

10. The method of claim 1, wherein the density of contact points between the nanofibers and the second surface of the second article comprises contact of from at least about 5 nanofibers per micron$^2$ to 1000 nanofibers per micron$^2$.

11. The method of claim 1, wherein the density of contact points between the nanofibers and the second surface of the second article comprises contact of from at least about 10 nanofibers per micron$^2$ to 500 nanofibers per micron$^2$.

12. The method of claim 1, wherein the density of contact points between the nanofibers and the second surface of the second article comprises contact of from at least about 50 nanofibers per micron$^2$ to 250 nanofibers per micron$^2$.

13. The method of claim 1, wherein the density of contact points between the nanofibers and the second surface of the second article comprises contact of from at least about 75 nanofibers per micron$^2$ to 150 nanofibers per micron$^2$.

14. The method of claim 1, further comprising depositing a second plurality of inorganic nanofibers on the first surface of the first article, wherein the second plurality of nanofibers have a straight configuration.

* * * * *